(12) United States Patent
Pansky et al.

(10) Patent No.: US 12,082,839 B2
(45) Date of Patent: Sep. 10, 2024

(54) WORKING CHANNEL DEVICE

(71) Applicant: T.A.G. Medical Products Corporation Ltd., Kibbutz Gaaton (IL)

(72) Inventors: Amir Pansky, Atlit (IL); Ben Zion Spector, Tel-Mond (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 813 days.

(21) Appl. No.: 17/041,040

(22) PCT Filed: Jun. 29, 2020

(86) PCT No.: PCT/IL2020/050723
§ 371 (c)(1),
(2) Date: Sep. 24, 2020

(87) PCT Pub. No.: WO2022/003659
PCT Pub. Date: Jan. 6, 2022

(65) Prior Publication Data
US 2021/0100576 A1    Apr. 8, 2021

Related U.S. Application Data

(63) Continuation-in-part of application No. 16/362,971, filed on Mar. 25, 2019, now Pat. No. 11,478,234.
(Continued)

(51) Int. Cl.
*A61B 1/018*  (2006.01)
*A61B 1/005*  (2006.01)
(Continued)

(52) U.S. Cl.
CPC .... *A61B 17/32002* (2013.01); *A61B 17/1631* (2013.01); *A61B 17/1633* (2013.01); *A61B 2017/320032* (2013.01)

(58) Field of Classification Search
CPC . A61B 1/018; A61B 1/005; A61B 17/320016; A61B 17/00234;
(Continued)

(56) References Cited

U.S. PATENT DOCUMENTS 5,395,367 A    3/1995  Wilk
7,678,117 B2   3/2010  Hinman et al.
(Continued)

FOREIGN PATENT DOCUMENTS

WO    WO 2022/003659    1/2022

OTHER PUBLICATIONS

International Search Report and the Written Opinion Dated Sep. 30, 2020 From the International Searching Authority Re. Application No. PCT/IL2020/05723. (8 Pages).
(Continued)

*Primary Examiner* — Anh T Dang

(57) ABSTRACT

An arthroscopic surgical device including: a body with a proximal end, a distal end, and a body longitudinal axis extending between the proximal end and the distal end; the body including: an elongated sheath arranged along a sheath longitudinal axis, the sheath including: a sheath flexible portion; and a lumen running longitudinally through the sheath; an elongated spine arranged along a spine longitudinal axis, the spine connected to the sheath, the spine including a spine joint; wherein the spine is rigid in a direction of elongation of the spine; wherein the sheath longitudinal axis and the spine longitudinal axis are aligned, for at least a portion of a sheath longitudinal length, wherein the flexible portion axially overlaps with the spine joint, bending the spine joint thereby bending the flexible portion.

27 Claims, 24 Drawing Sheets

Related U.S. Application Data

(60) Provisional application No. 62/647,752, filed on Mar. 25, 2018.

(51) Int. Cl.
 A61B 17/00 (2006.01)
 A61B 17/16 (2006.01)
 A61B 17/32 (2006.01)

(58) Field of Classification Search
 CPC ...... A61B 2017/00292; A61B 1/00087; A61B 1/045; A61B 1/0125; A61B 1/0051; A61B 1/0052; A61B 2017/320024; A61B 2017/00305; A61B 1/00101; A61B 1/00085; A61B 1/00098; A61B 1/0014; A61B 17/29; A61B 17/2909; A61B 2017/2927; A61B 2017/2905; A61B 2017/2908; A61B 17/32056
 See application file for complete search history.

(56) References Cited

U.S. PATENT DOCUMENTS

| | | |
|---|---|---|
| 8,926,597 B2 | 1/2015 | Lee |
| 9,005,112 B2 | 4/2015 | Hasser et al. |
| 10,245,029 B2 | 4/2019 | Hunter et al. |
| 10,617,438 B2 | 4/2020 | O'Keefe et al. |
| 11,278,234 B2 | 3/2022 | Maletic |
| 11,478,234 B2 | 10/2022 | Pansky et al. |
| 2007/0021737 A1 | 1/2007 | Lee |
| 2008/0051802 A1 | 2/2008 | Schostek et al. |
| 2008/0183035 A1 | 7/2008 | Vakharia et al. |
| 2016/0074056 A1 | 3/2016 | Conlon |
| 2016/0081714 A1 | 3/2016 | Kobayashi et al. |
| 2017/0065290 A1* | 3/2017 | Smith .............. A61B 17/00234 |
| 2020/0315436 A1 | 10/2020 | Pansky et al. |
| 2023/0101124 A1 | 3/2023 | Pansky et al. |

OTHER PUBLICATIONS

International Preliminary Report on Patentability Dated Jan. 12, 2023 From the International Bureau of WIPO Re. Application No. PCT/ IL2020/050723. (8 Pages).
Official Action Dated Jan. 6, 2022 from US Patent and Trademark Office Re. U.S. Appl. No. 16/362,971. (16 pages).
Notice of Allowance Dated Jun. 24, 2022 from US Patent and Trademark Office Re. U.S. Appl. No. 16/362,971. (7 pages).
Official Action Dated Nov. 12, 2020 From the US Patent and Trademark Office Re. U.S. Appl. No. 16/362,971. (9 Pages).
Final Official Action Dated May 21, 2021 From the US Patent and Trademark Office Re. U.S. Appl. No. 16/362,971. (21 Pages).
Supplementary European Search Report and the European Search Opinion Dated Feb. 2, 2024 From the European Patent Office Re. Application No. 20942767.3. (9 Pages).
Official Action Dated Feb. 7, 2024 From the US Patent and Trademark Office Re. U.S. Appl. No. 17/966,977. (24 Pages).

* cited by examiner

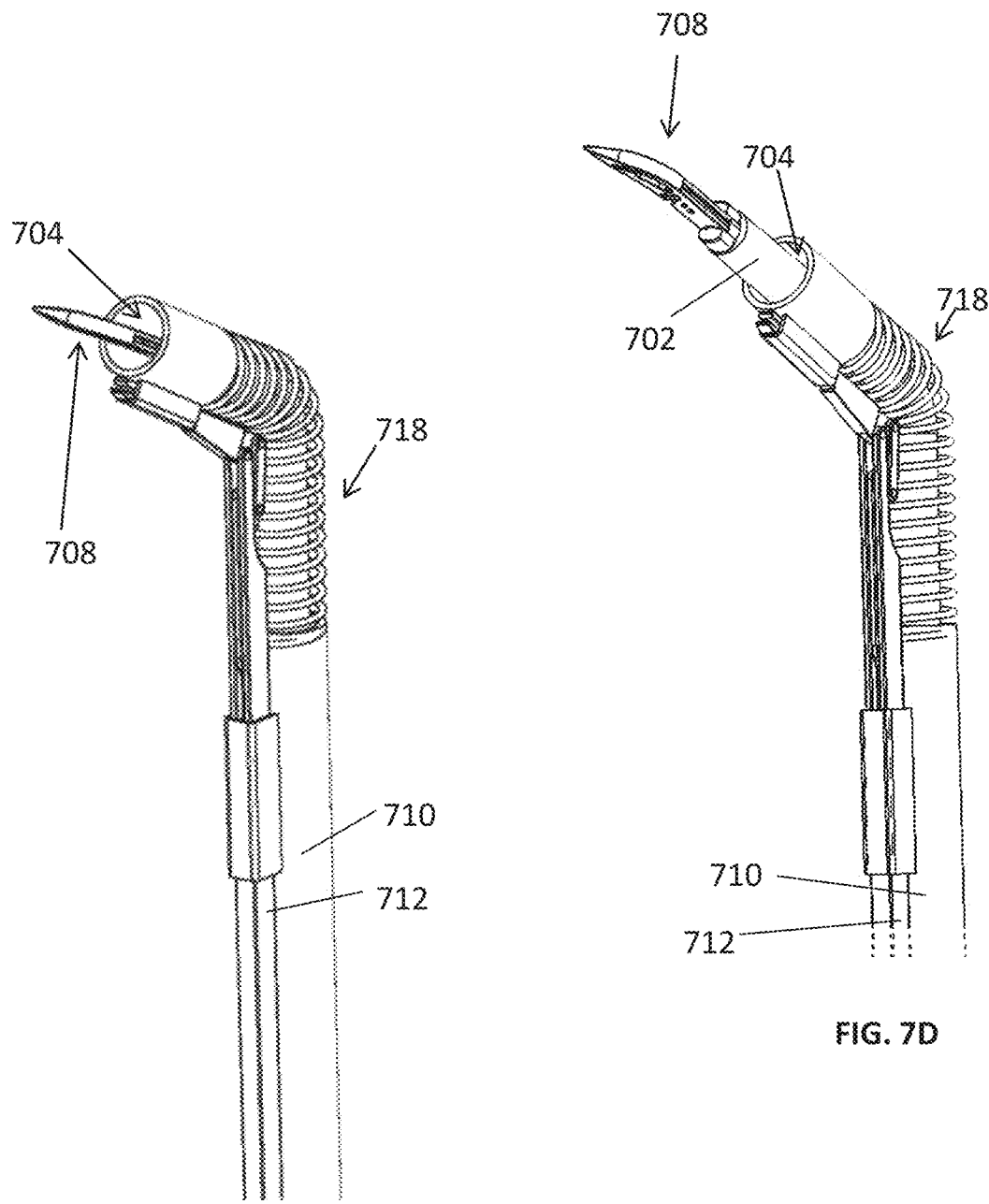

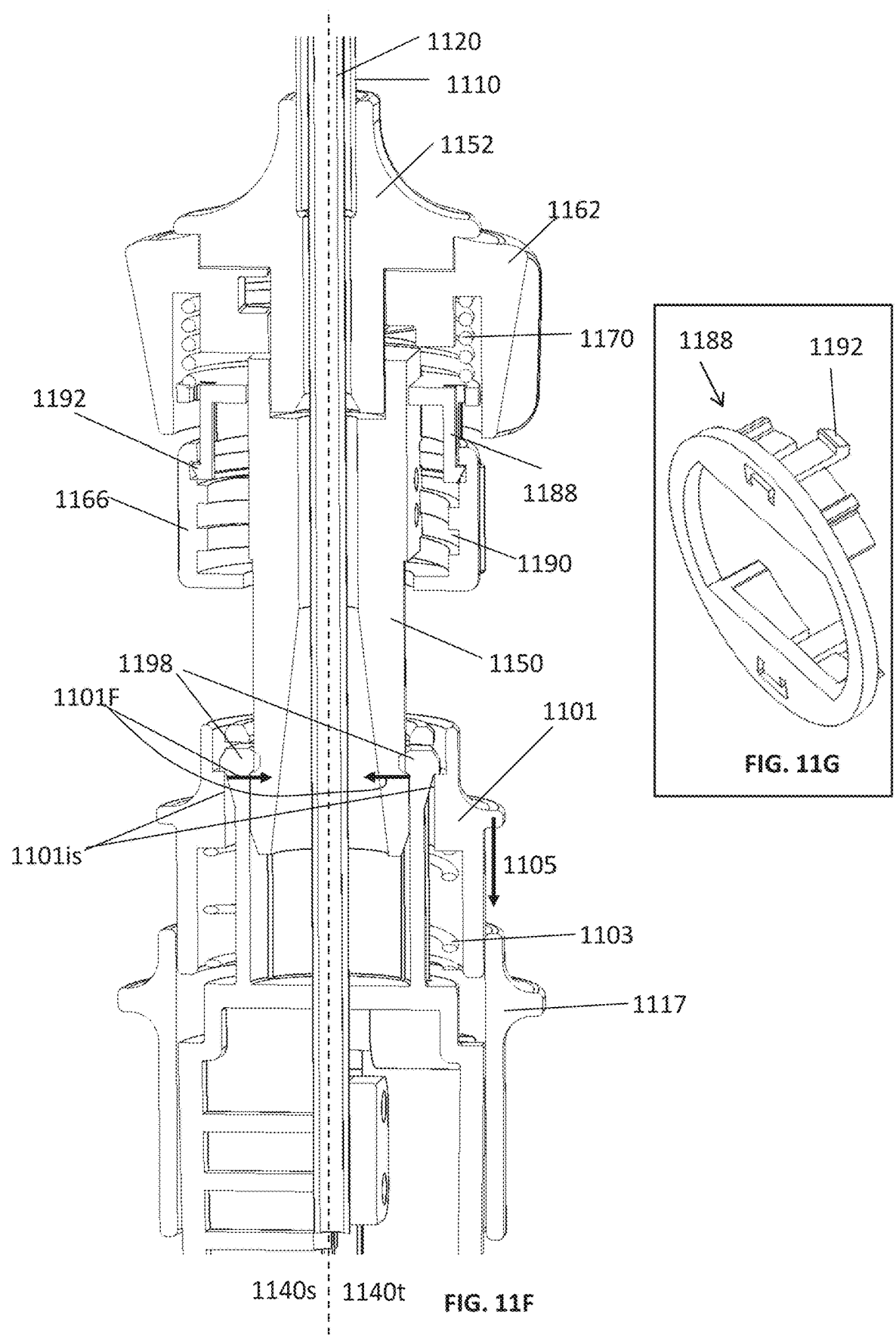

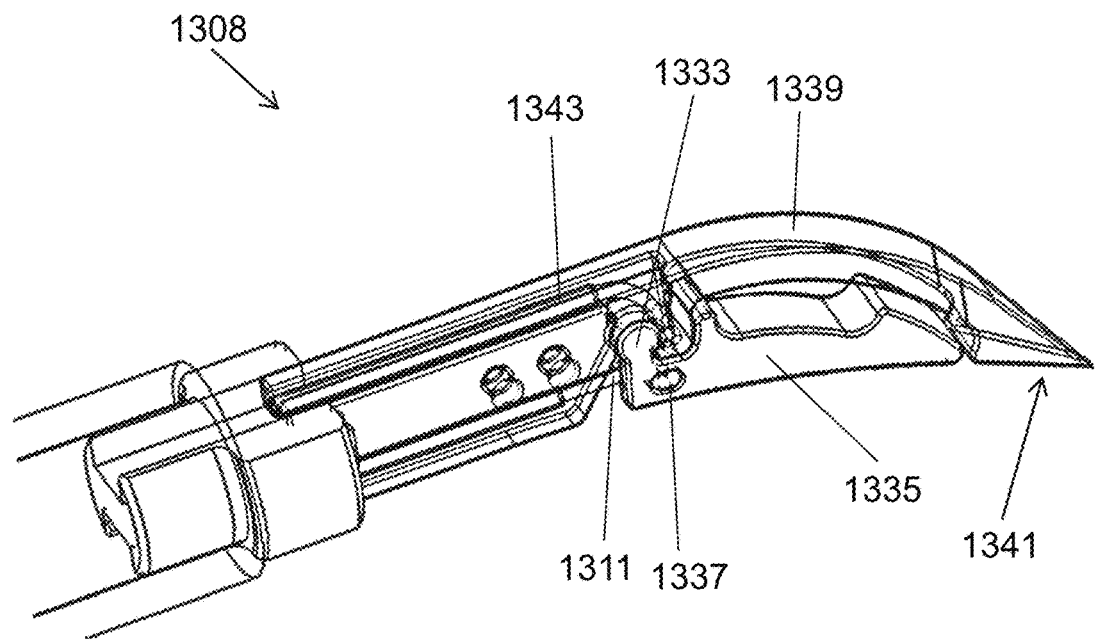
FIG. 13
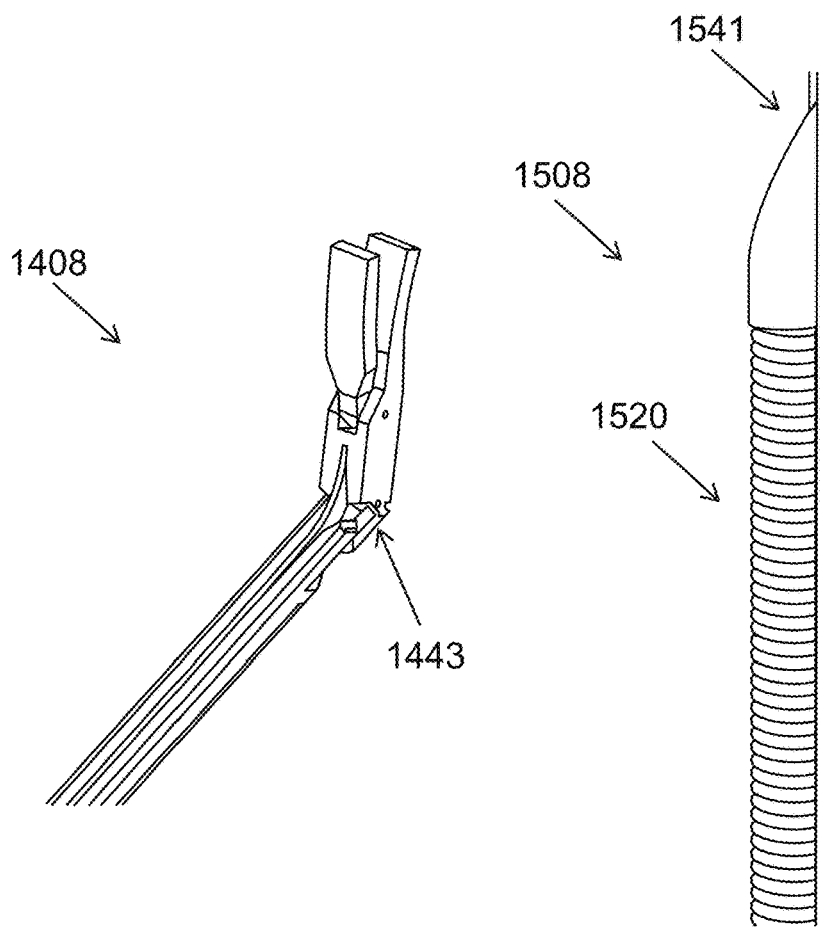
FIG. 14
FIG. 15

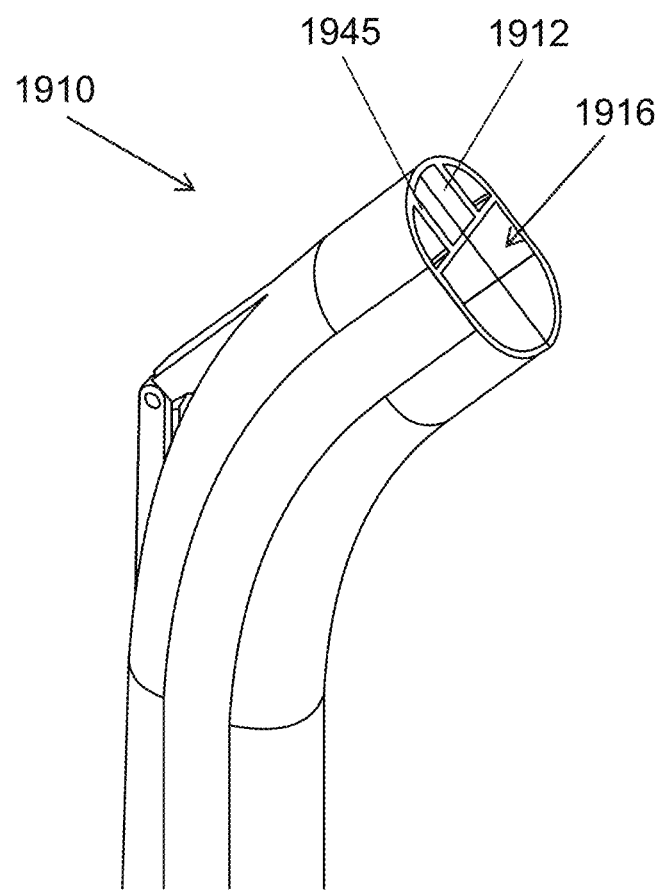
FIG. 19
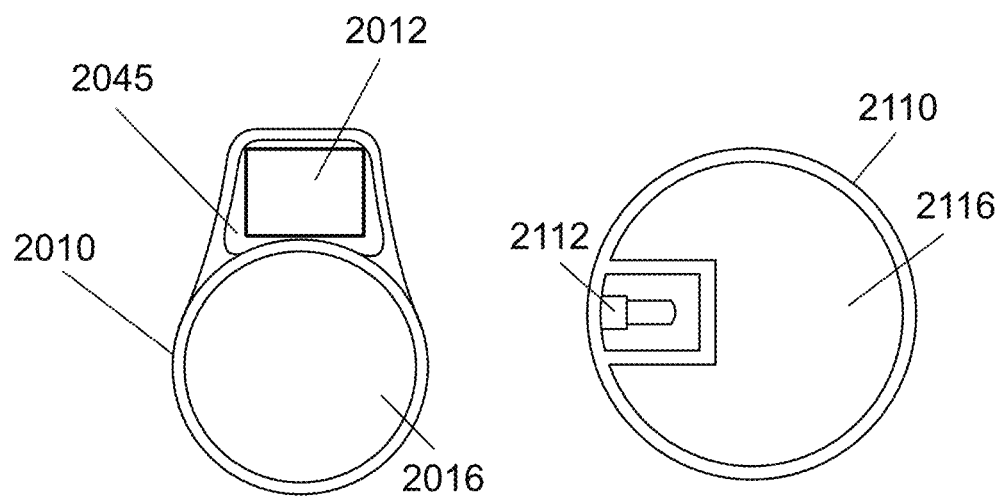
FIG. 20
FIG. 21

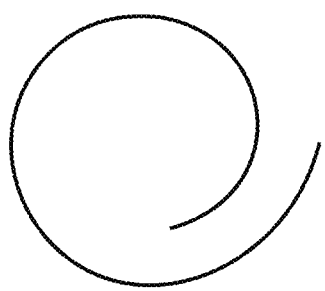
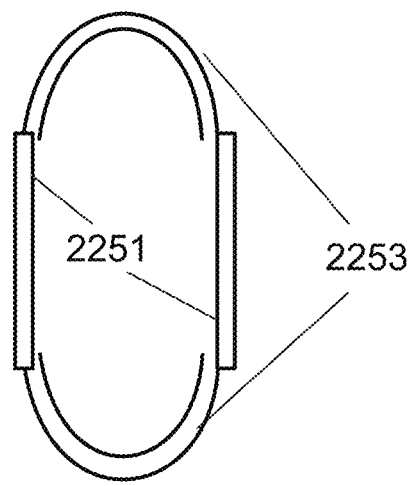
FIG. 22A
FIG. 22B
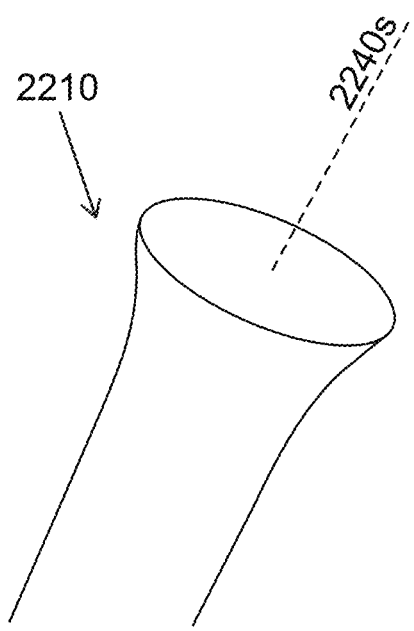
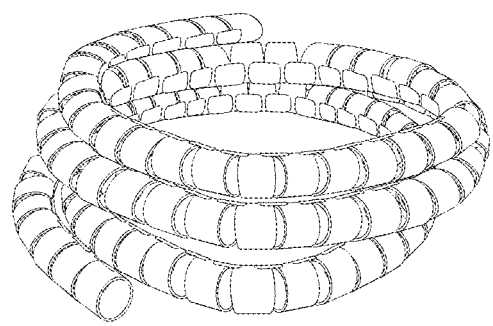
FIG. 22C
FIG. 22D

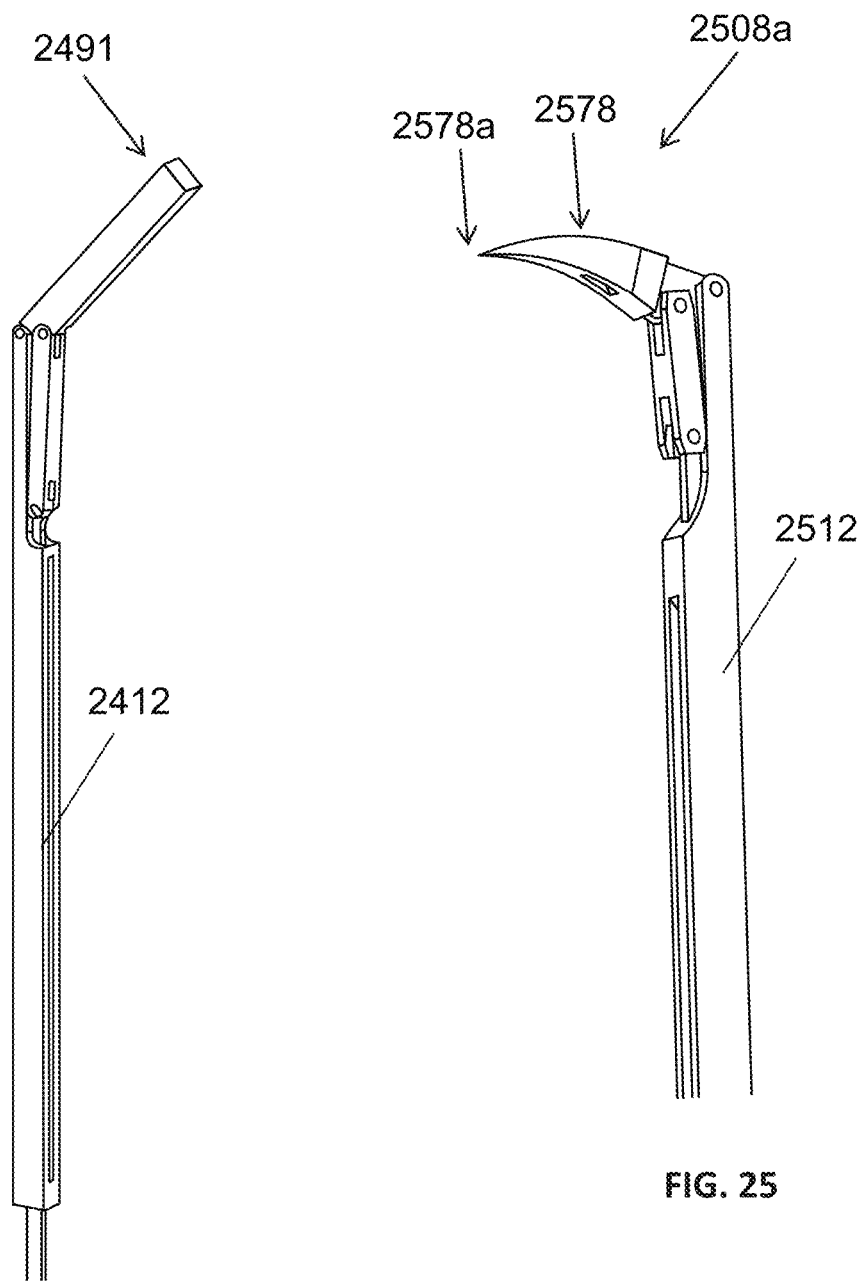

WORKING CHANNEL DEVICE

RELATED APPLICATIONS

This application is a National Phase of PCT Patent Application No. PCT/IL2020/050723 having International filing date of Jun. 29, 2020, which is a Continuation-in-Part (CIP) of U.S. patent application Ser. No. 16/362,971 filed on Mar. 25, 2019, which claims the benefit of priority under 35 USC § 119(e) of U.S. Provisional Patent Application No. 62/647,752 filed on Mar. 25, 2018. The contents of the above applications are all incorporated by reference as if fully set forth herein in their entirety.

FIELD AND BACKGROUND OF THE INVENTION

The present invention, in some embodiments thereof, relates to a surgical tool and, more particularly, but not exclusively, to an arthroscopic tool for meniscus surgery.

Background art includes U.S. Pat. No. 5,391,180, U.S. Pat. No. 7,8159091, U.S. Pat. No. 7,815,091, US Patent Application No. 20150080933, U.S. Pat. No. 5,331,948, U.S. Pat. No. 8,771,260, US Patent Application No. 20110275901, US Patent Application No. 20090177041, and US Patent Application No. 20140246472.

SUMMARY OF THE INVENTION

The present invention, in some embodiments thereof, relates to a surgical tool and, more particularly, but not exclusively, to an arthroscopic tool for meniscus surgery.

Following is a non-exclusive list including some examples of embodiments of the invention. The invention also includes embodiments which include fewer than all the features in an example and embodiments using features from multiple examples, also if not expressly listed below.

Example 1. An arthroscopic surgical device comprising:
a body with a proximal end, a distal end, and a body longitudinal axis extending between said proximal end and said distal end;
said body comprising:
an elongated sheath arranged along a sheath longitudinal axis, said sheath comprising:
a sheath flexible portion; and
a lumen running longitudinally through said sheath;
an elongated spine arranged along a spine longitudinal axis, said spine connected to said sheath, said spine comprising a spine joint;
wherein said spine is rigid in a direction of elongation of said spine;
wherein said sheath longitudinal axis and said spine longitudinal axis are aligned, for at least a portion of a sheath longitudinal length,
wherein said flexible portion axially overlaps with said spine joint, bending said spine joint thereby bending said flexible portion.

Example 2. The arthroscopic surgical device of Example 1, wherein said lumen is sized and shaped to receive an arthroscopic tool.

Example 3. The arthroscopic surgical device of any one of Examples 1-2, wherein said spine joint is positioned in a distal portion of the spine.

Example 4. The arthroscopic surgical device of any one of Examples 1-3, wherein said spine joint is positioned within a distal 20% of a length of the spine.

Example 5. The arthroscopic surgical device of any one of Examples 1-4, a longitudinal length of said flexible portion is 1-5% of said sheath longitudinal length.

Example 6. The arthroscopic surgical device of any one of Examples 1-5, wherein a maximal extent, perpendicular to said body longitudinal axis, of a distal portion of said body is less than 5 mm.

Example 7. The arthroscopic surgical device of Example 6, wherein said distal portion is a distal 20% of a length of said body.

Example 8. The arthroscopic surgical device of any one of Examples 1-7, wherein said sheath longitudinal axis and said spine longitudinal axis are aligned for at least a distal 20% of a length of the sheath.

Example 9. The arthroscopic surgical device of any one of Examples 1-8, wherein when a proximal end of said spine is held in a fixed position and 20 g is applied in direction perpendicular to said spine longitudinal axis at a distal end of the spine, the spine deflects, a body of said spine deflecting said body from a straight configuration by less than 1 degree.

Example 10. The arthroscopic surgical device of any one of Examples 1-9, wherein said spine joint is less than 3 mm long in an axial direction.

Example 11. The arthroscopic surgical device of any one of Examples 1-10, wherein a radius of curvature of said joint, when said spine is bent at said joint, is less than 2 mm.

Example 12. The arthroscopic surgical device of any one of Examples 1-11, wherein said spine joint is a pivot joint.

Example 13. The arthroscopic surgical device of any one of Examples 1-12, wherein said spine joint is bendable, from a straight orientation in a single bending plane, by 0-130°.

Example 14. The arthroscopic surgical device of any one of Examples 1-13, wherein said sheath flexible portion is radially expandable.

Example 15. The arthroscopic surgical device of any one of Examples 1-14, wherein said spine comprises:
a first elongated spine rod;
a second elongated spine rod;
a distal portion of the spine, where said distal portion:
is attached to a distal end of said first spine rod at a first point on said distal portion; and
is attached to said second spine rod at a second point on said distal portion, spaced from said first point;
where relative axial movement between said first and said second spine rods changes an angle of said distal portion with respect to long axes of said first and said second spine rod.

Example 16. The arthroscopic surgical device of Example 15, comprising a first pivot joint, wherein said distal end of said first spine rod is pivotally attached at said first pivot joint to said distal portion.

Example 17. The arthroscopic surgical device of Example 16, comprising a second pivot joint, wherein said distal end of said second spine rod is pivotally attached at said second pivot joint to said distal portion.

Example 18. The arthroscopic surgical device of any one of Examples 15-17, wherein said second spine rod is at least partially housed within a lumen of said first spine rod.

Example 19. The arthroscopic surgical device of any one of Examples 15-18, wherein relative movement between said first and said second spine rod is actuated at proximal portions of said rods.

Example 20. The arthroscopic surgical device of any one of Examples 1-19, wherein said elongated sheath comprises a first sheath portion and a second sheath portion;

wherein said second sheath portion is sized and shaped to cover a distal portion of said first sheath portion and extend distally therefrom; and where said elongated spine is connected to said first sheath portion.

Example 21. An arthroscopic surgical device system comprising:
the arthroscopic surgical device of any one of Examples 1-20; and an elongated surgical tool sized and shaped to move axially within said lumen.

Example 22. The arthroscopic surgical device system of Example 21, wherein said surgical tool is elongated.

Example 23. The arthroscopic surgical device system of any one of Examples 21-22, wherein said surgical tool comprises a tool flexible portion.

Example 24. The arthroscopic surgical device system of any one of Examples 21-23, wherein a body of said surgical tool is flexible along a majority of a length of said surgical tool.

Example 25. The arthroscopic surgical device system of any one of Examples 21-24, wherein said surgical tool is axially moveable with respect to said sheath, to position said tool flexible portion in an axially overlapping position with said sheath flexible portion.

Example 26. The arthroscopic surgical device system of Example 25, wherein said surgical tool is rotatable around a surgical tool longitudinal axis when a portion of said surgical tool is disposed within said lumen.

Example 27. The arthroscopic surgical device system of any one of Examples 21-26, comprising a lock which locks bending of said spine.

Example 28. The arthroscopic surgical device system of any one of Examples 21-27, comprising a lock which locks axial movement of said surgical tool with respect to said sheath.

Example 29. The arthroscopic surgical device system of any one of Examples 21-28, comprising a controller for bending of said spine, located at a handle located at proximal portion of said system.

Example 30. The arthroscopic surgical device system of Example 29, where said tool comprises an end effector;
wherein said surgical device system comprises a controller for actuation of said end effector located at said handle.

Example 31. The arthroscopic surgical device system of any one of Examples 29-30, wherein one or more locks for locking of bending of said spine and locking of axial movement of said tool with respect to said sheath are located in said handle.

Example 32. An arthroscopic surgical device comprising:
an elongated spine, said elongated spine axially rigid and comprising a joint positioned within a distal 20% of a length of the spine; and
an surgical tool connected to said elongated spine, said tool comprising a flexible portion, where coupling between said surgical tool and said spine allows axial alignment between said joint and said flexible portion.

Example 33. The arthroscopic surgical device of Example 32, wherein said coupling comprises an elongated sheath.

Example 34. A method of arthroscopic treatment comprising:
positioning an outlet of an working channel device within tissue of a subject;
bending said working channel device to reposition said outlet; and treating tissue at a treatment site within tissue of said subject with an arthroscopic tool accessing said treatment site from a lumen of said working channel and through said outlet.

Example 35. The method of Example 34, wherein said treatment site is within a joint of said subject.

Example 36. The method of Example 35, wherein said working channel device comprises a sheath rigidized by a spine comprising a spine joint, where said outlet is an outlet of said sheath; and
wherein said bending comprises bending said spine at said spine joint to bend said sheath.

Example 37. A kit for arthroscopic treatment comprising:
the arthroscopic surgical device of any one of Examples 1-20; and
a plurality of elongated surgical tools sized and shaped to move axially within said lumen.

Example 38. The kit for arthroscopic treatment of Example 37, wherein said elongated sheath comprises a first sheath portion and a second sheath portion;
wherein said second sheath portion is sized and shaped to cover a distal portion of said first sheath portion and extend distally therefrom; and
where said elongated spine is connected to said first sheath portion.

Example 39. The kit of Example 38, wherein said first sheath portion is rigid and wherein said sheath flexible portion is part of said second sheath portion.

Example 40. The kit of Example 39, wherein said first sheath portion and said spine are steralizable.

Example 41. The kit of Example 40, comprising a plurality of said second sheath portions.

Example 42. An arthroscopic surgical device comprising:
a body with a proximal end, a distal end, and a body running between said proximal end and said distal end;
said body comprising:
an elongated sheath running lengthwise with respect to said body and comprising:
a sheath flexible portion; and
a lumen running longitudinally through said sheath;
an elongated spine running lengthwise with respect to said body, said spine connected to said sheath and said spine comprising a spine joint;
wherein said spine is rigid in a direction of elongation of said spine;
wherein said sheath and said spine longitudinal are aligned running along a direction of elongation of the sheath, for at least a portion of a sheath length,
wherein said flexible portion overlaps lengthwise with said spine joint, bending said spine joint thereby bending said flexible portion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 7A:
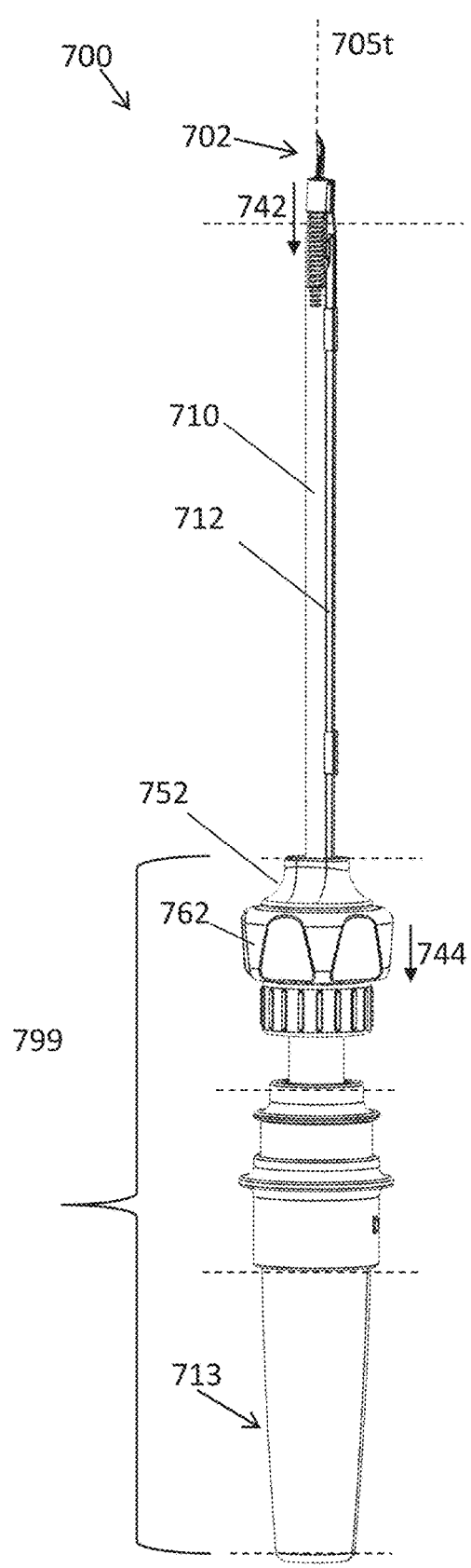
Figure 7B:
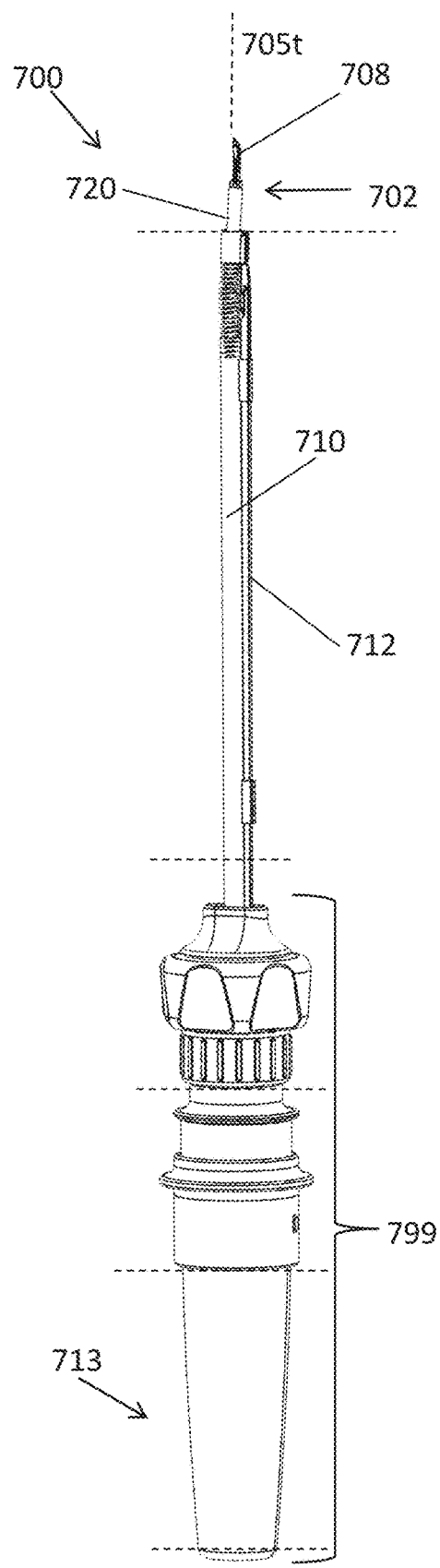
Figure 8A:
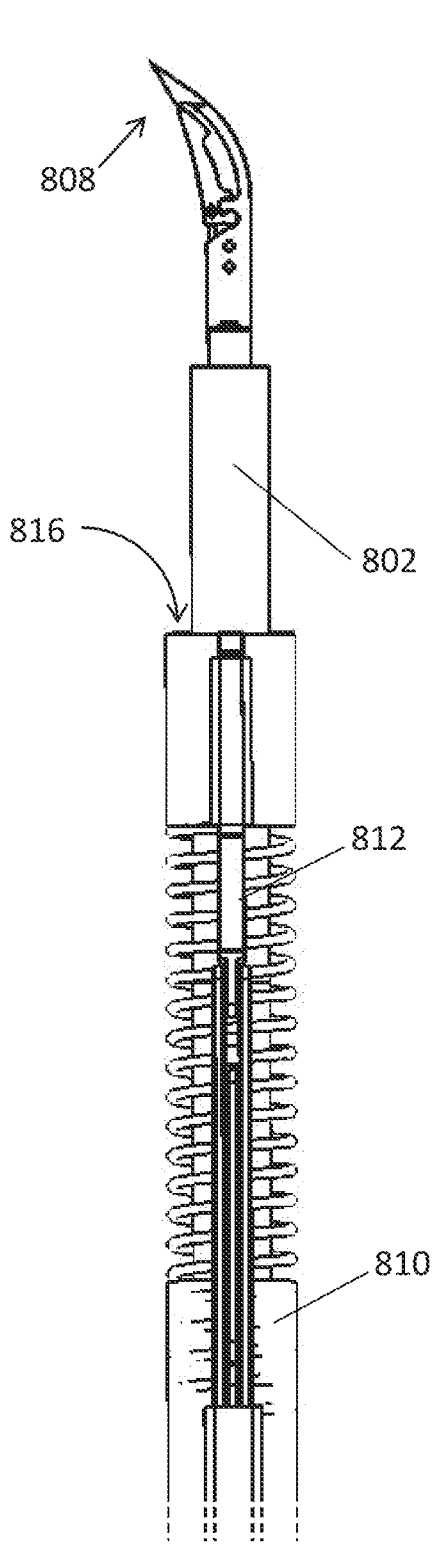
Figure 8B:
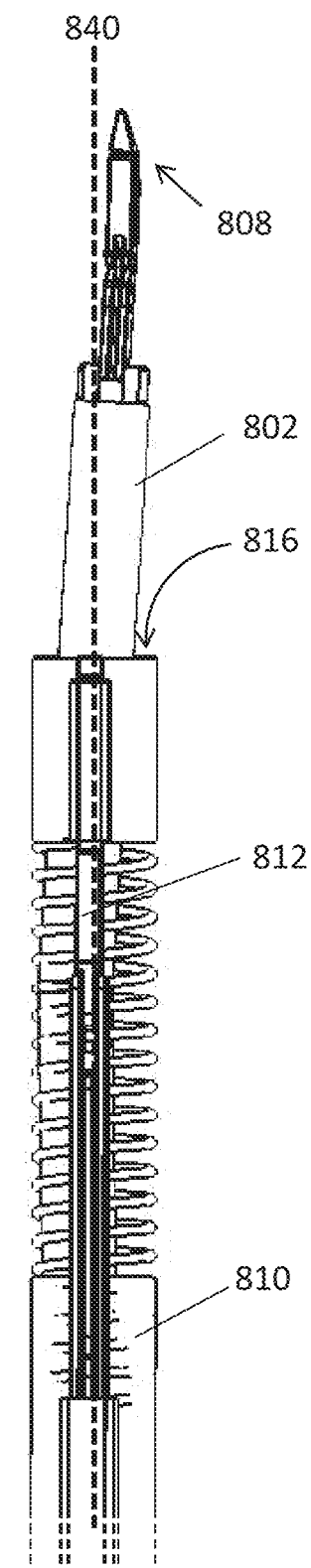
Figure 9:
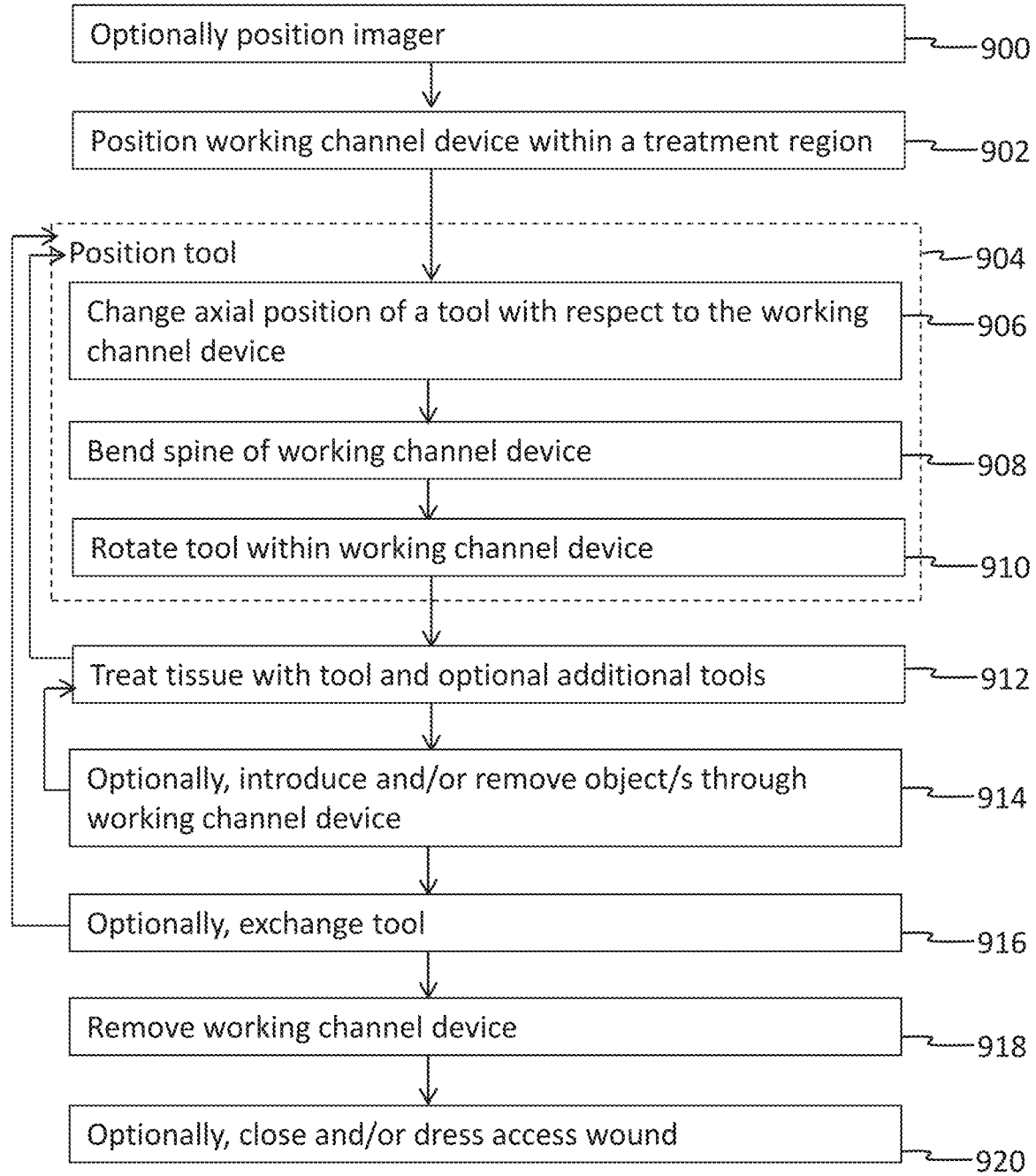
Figure 11A:
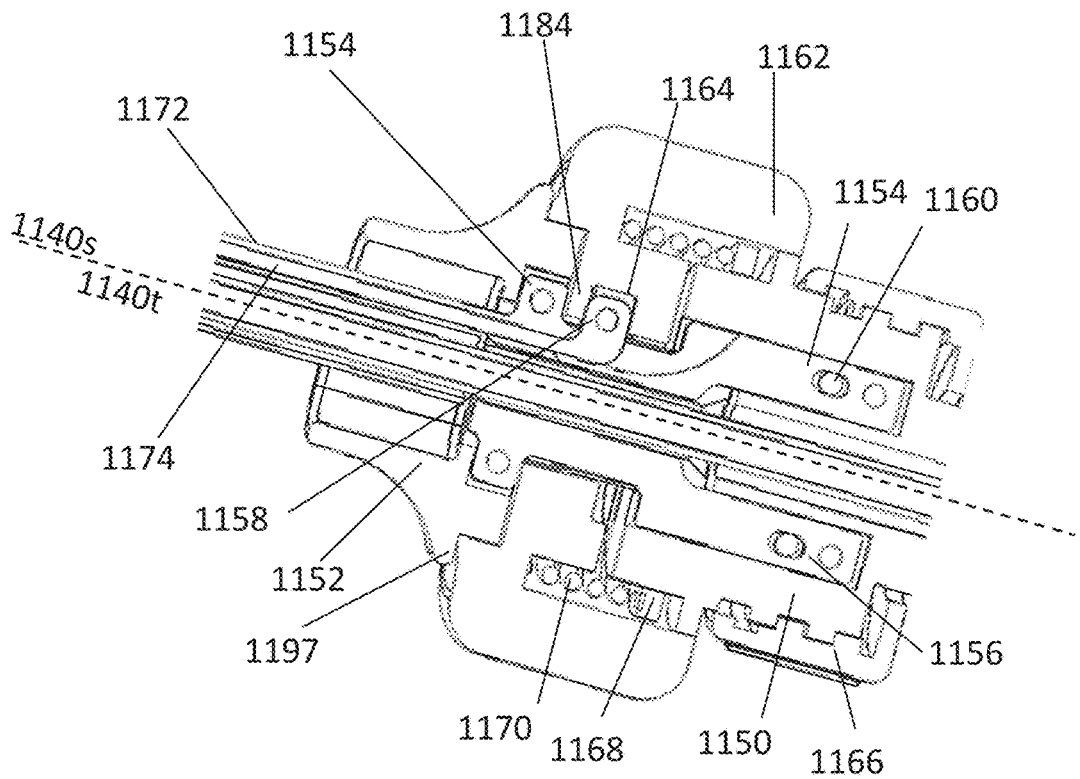
Figure 11B:
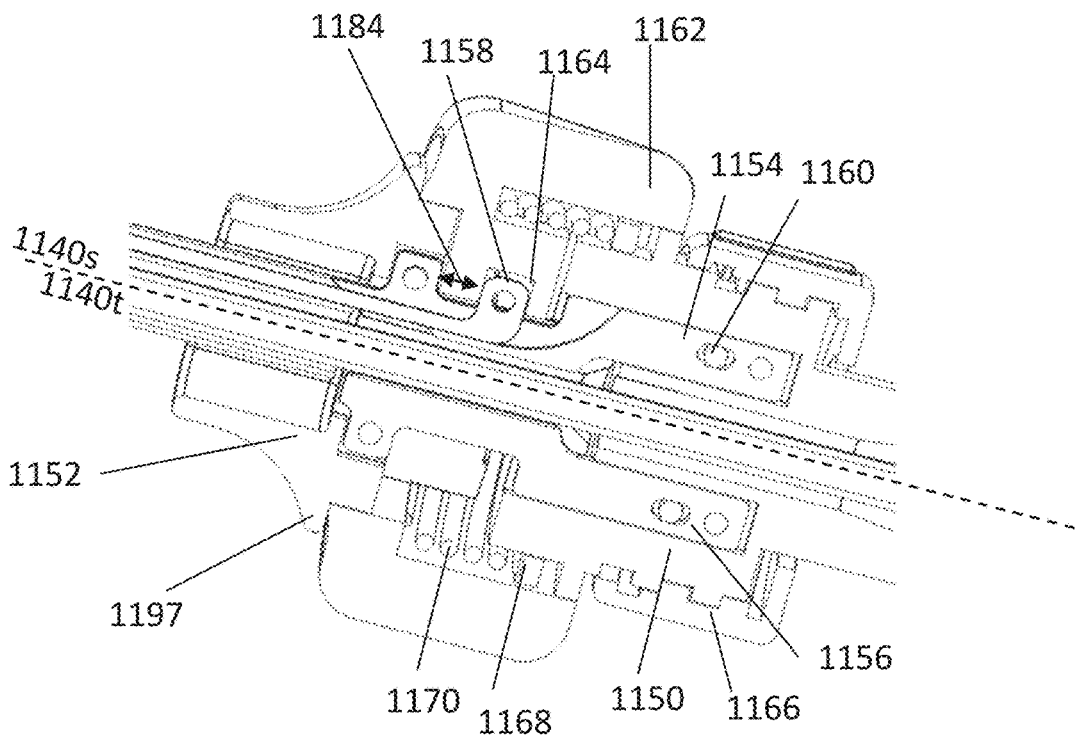
Figure 11C:
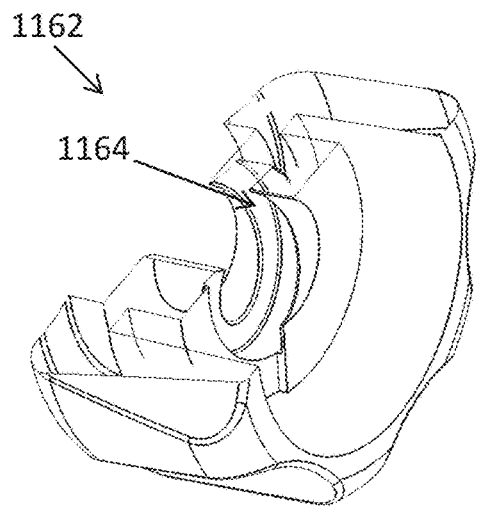
Figure 11D:
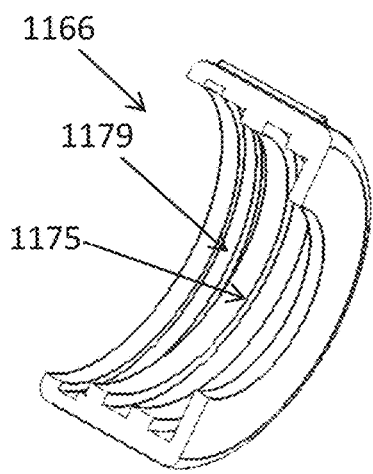
Figure 11E:
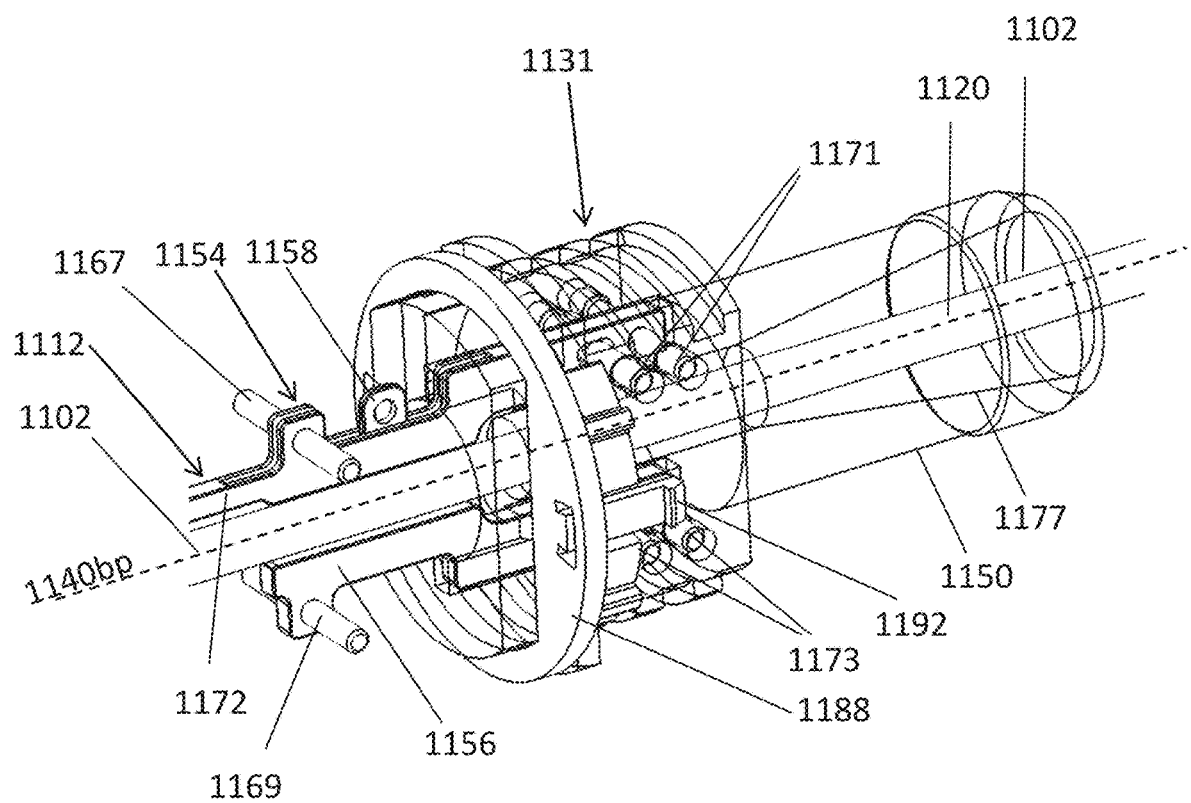
Figure 12A:
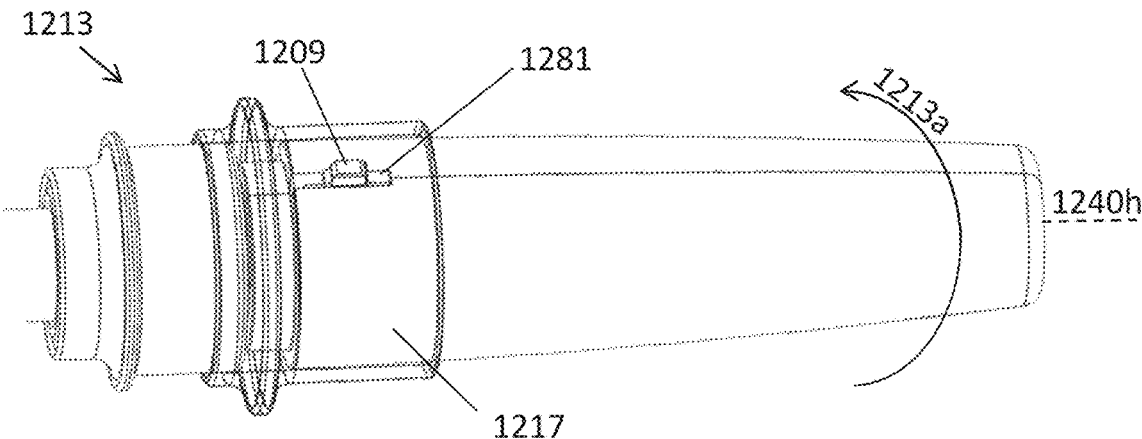
Figure 12B:
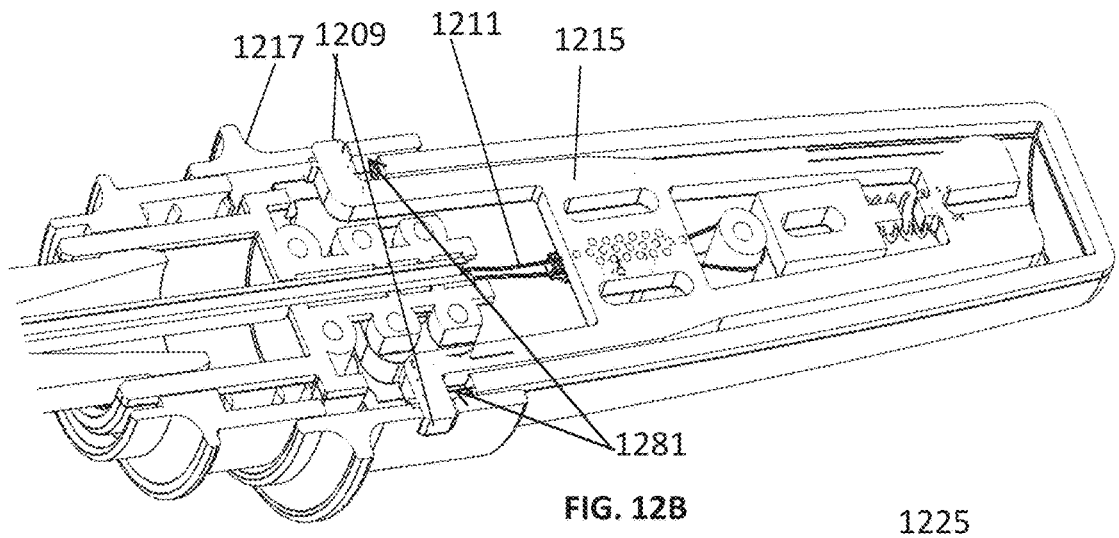
Figure 12C:
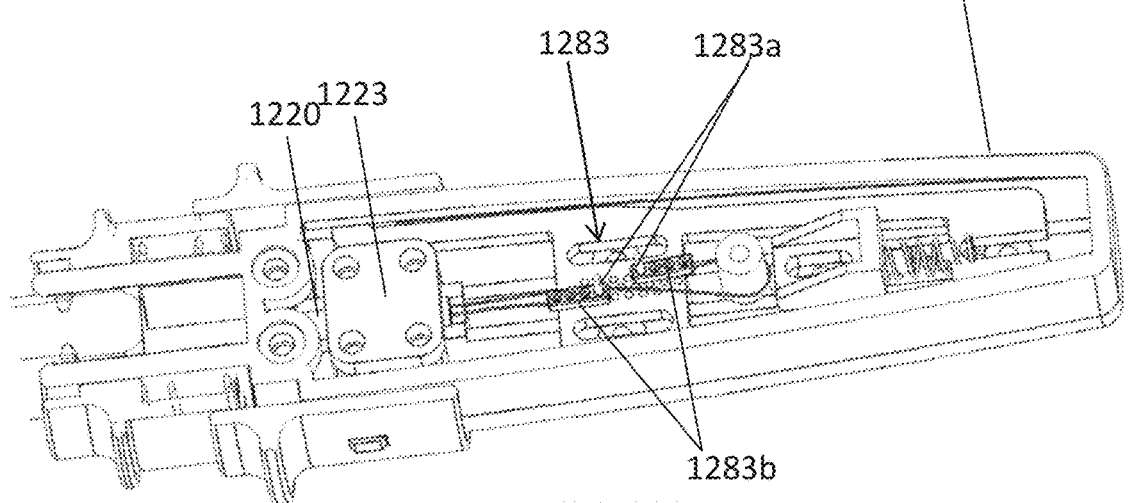

FIGS. 7A-B are simplified schematics of a device according to some embodiments of the invention;

FIGS. 7C-D are simplified schematics of a distal end of a device, according to some embodiments of the invention;

FIGS. 8A-B are simplified schematics of a distal end of a device 800, according to some embodiments of the invention;

FIG. 9 is a detailed method of treatment, according to some embodiments of the invention;

FIGS. 10A-E are simplified schematics of spine portions, according to some embodiments of the invention;

FIG. 11A-B are simplified schematic section views of a portion of a device, according to some embodiments of the invention;

FIG. 11C is a simplified schematic section view of a spine actuation knob 1162, according to some embodiments of the invention;

FIG. 11D is a simplified schematic section view of a spine bending locking knob 1166 according to some embodiments of the invention;

FIG. 11E is a simplified schematic view of a base portion, according to some embodiments of the invention;

FIG. 11F is a simplified schematic sectional view of a portion of a working channel device, according to some embodiments of the invention;

FIG. 11G is a simplified view of a portion of a device, according to some embodiments of the invention;

FIG. 12A is a simplified schematic view of a working channel device handle, according to some embodiments of the invention;

FIG. 12B is a simplified schematic section view of a working channel device handle, according to some embodiments of the invention;

FIG. 12C is a simplified schematic section view of a working channel device handle, according to some embodiments of the invention.

Figure 12D:
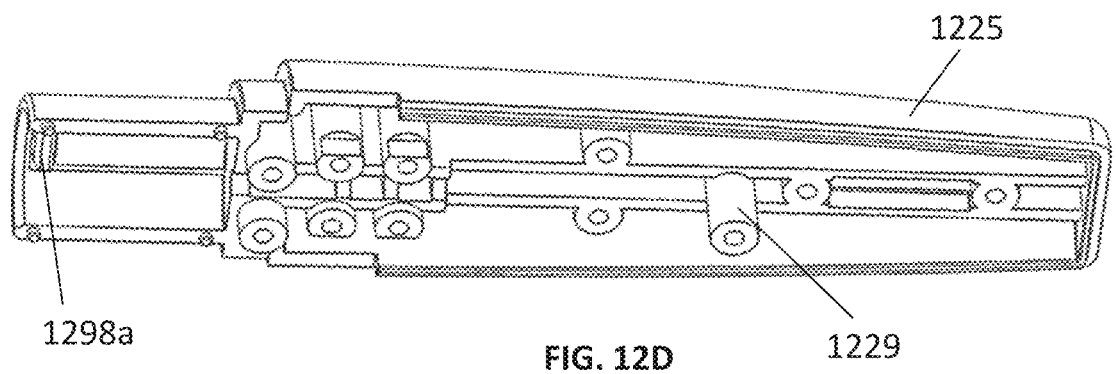
Figure 12E:
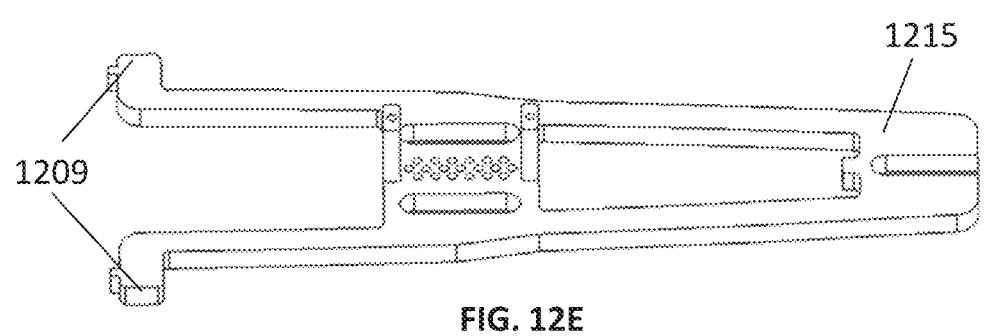
Figure 12F:
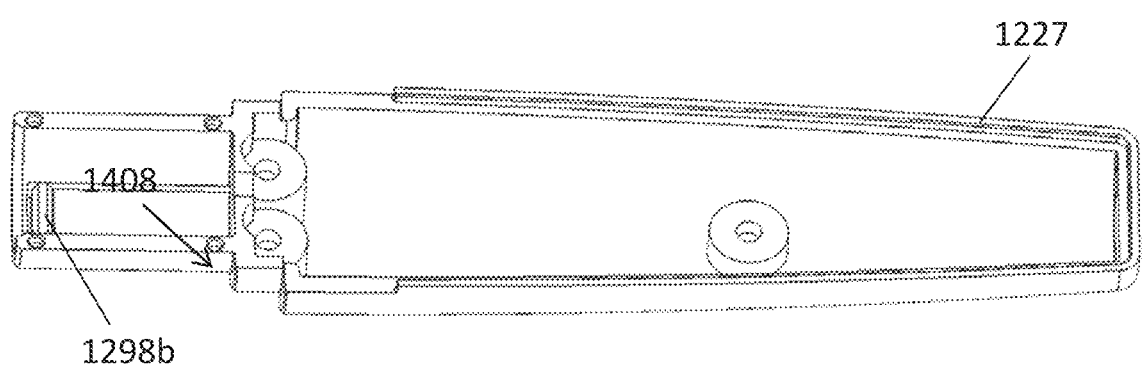
Figure 12G:
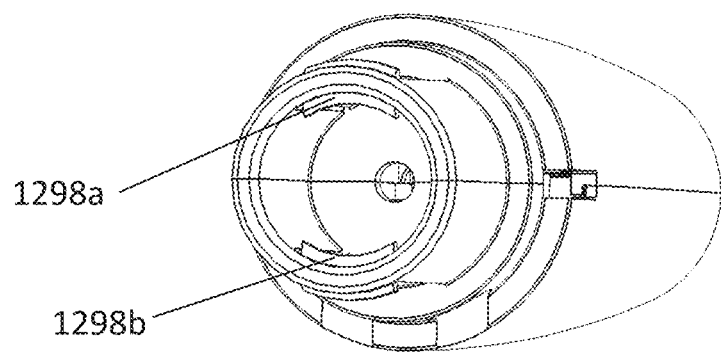
Figure 16:
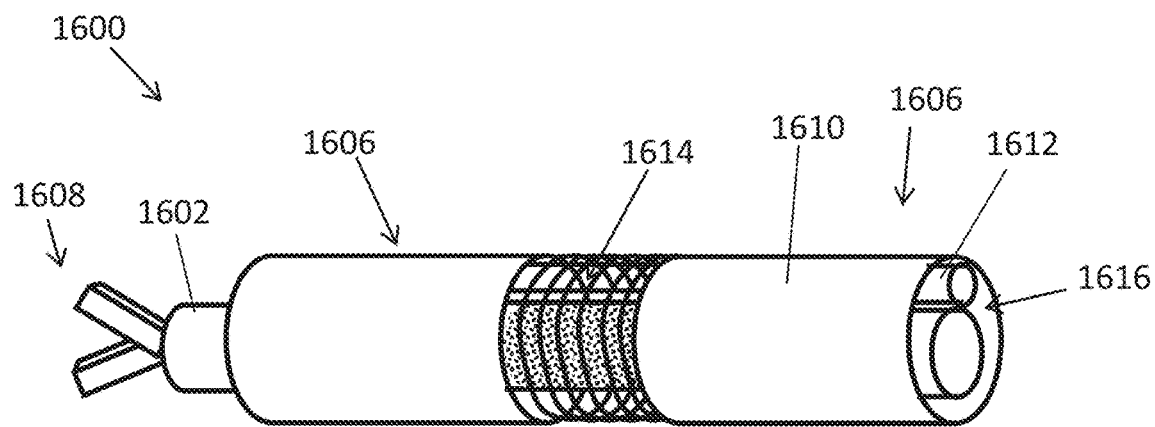
Figure 17:
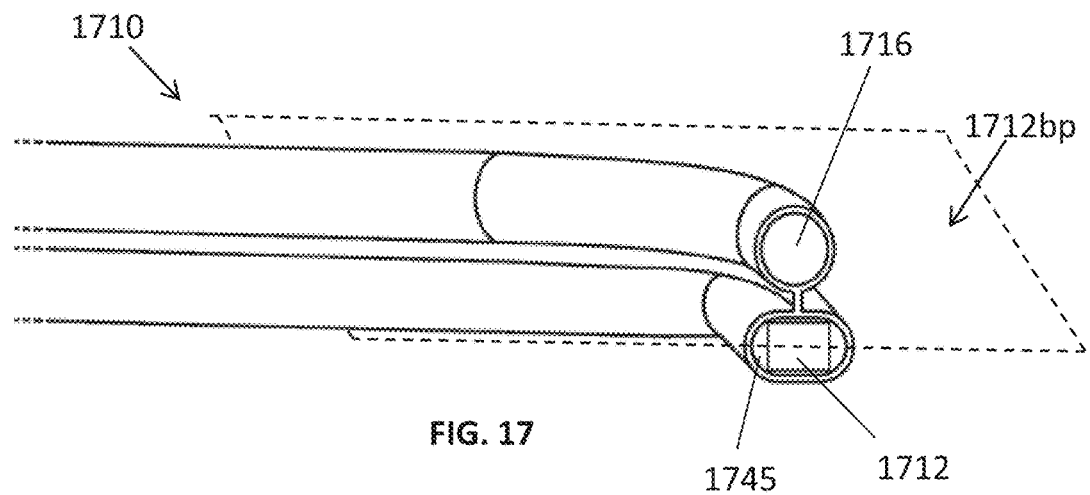
Figure 18:
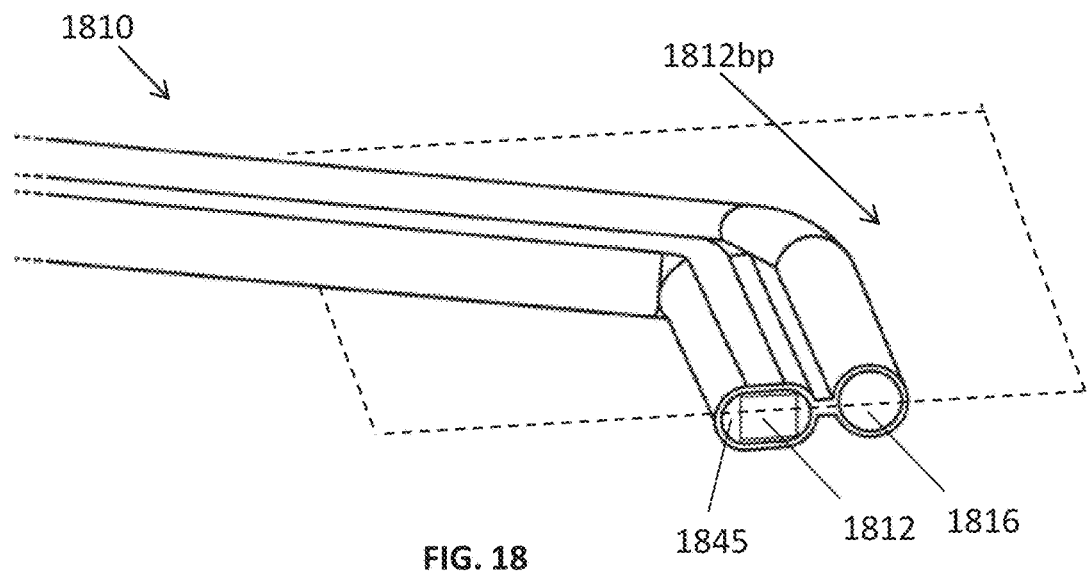
Figure 23A:
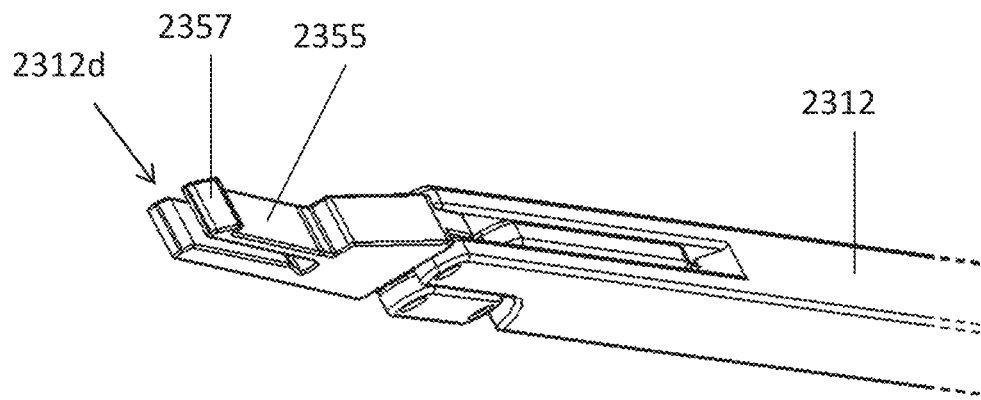
Figure 23B:
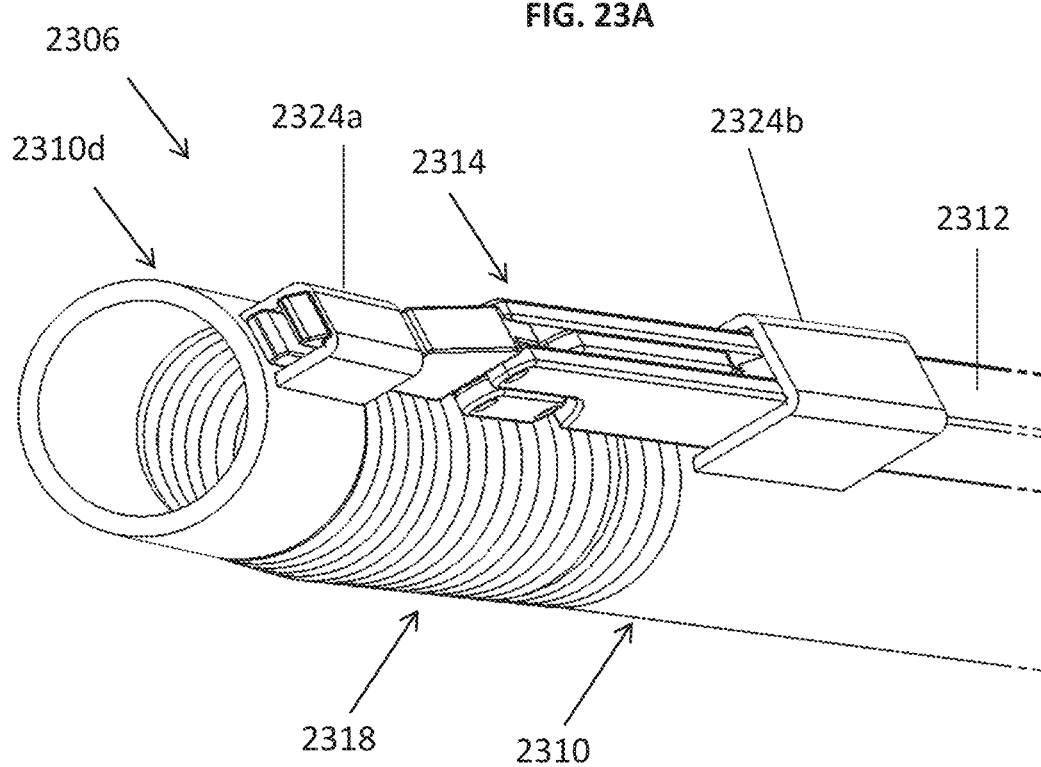
Figure 26:
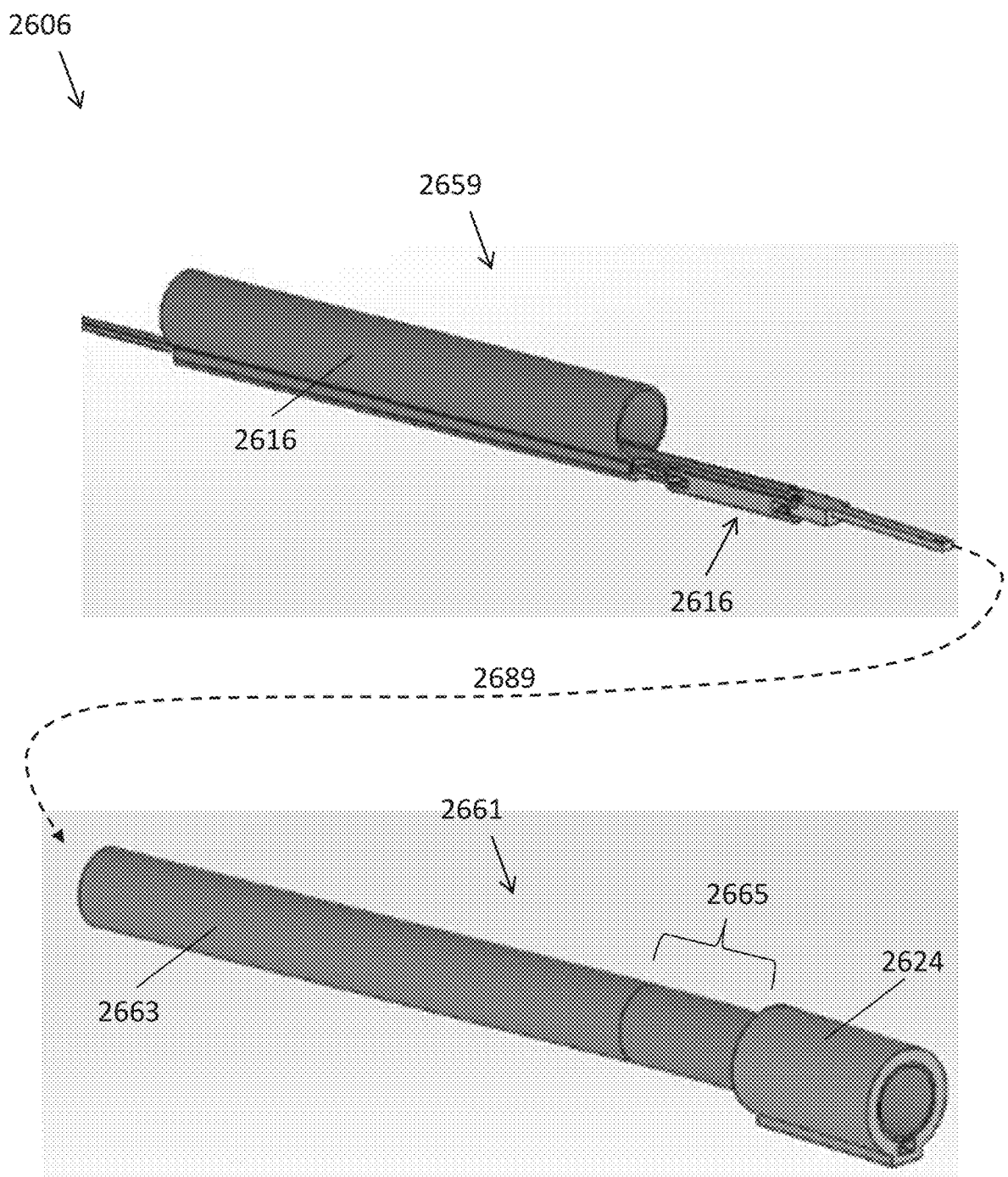

FIG. 12D is a simplified schematic view of a portion of a working channel device handle, according to some embodiments of the invention;

FIG. 12E is a simplified schematic view of a portion of a working channel device handle, according to some embodiments of the invention;

FIG. 12F is a simplified schematic view of a portion of a working channel device handle, according to some embodiments of the invention;

FIG. 12G is a simplified schematic view of a working channel device handle, according to some embodiments of the invention;

FIG. 13 is a simplified view of a tool end effector, according to some embodiments of the invention;

FIG. 14 is a simplified schematic of a grasper tool, according to some embodiments of the invention;

FIG. 15 is a simplified schematic of a needle tool, according to some embodiments of the invention;

FIG. 16 is a simplified schematic of a working channel device system, according to some embodiments of the invention;

FIG. 17 is a simplified schematic of a sheath, according to some embodiments of the invention;

FIG. 18 is a simplified schematic of a sheath, according to some embodiments of the invention;

FIG. 19 is a simplified schematic of a sheath, according to some embodiments of the invention;

FIG. 20 is a simplified schematic cross section of a sheath, according to some embodiments of the invention;

FIG. 21 is a simplified schematic cross section of a sheath, according to some embodiments of the invention;

FIGS. 22A-D are simplified schematics of sheath structures, according to some embodiments of the invention;

FIG. 23A is a simplified schematic of a distal portion of a spine, according to some embodiments of the invention;

FIG. 23B is a simplified schematic of a distal portion of a working channel device;

FIG. 24 is a simplified schematic of a distal portion of a spine, according to some embodiments of the invention;

FIG. 25 is a simplified schematic of a distal portion of a spine, according to some embodiments of the invention; and FIG. 26 is a simplified schematic of an exploded view of a working channel device, according to some embodiments of the invention.

DESCRIPTION OF SPECIFIC EMBODIMENTS OF THE INVENTION

The present invention, in some embodiments thereof, relates to a surgical tool and, more particularly, but not exclusively, to an arthroscopic tool for meniscus surgery.

Overview

A broad aspect of some embodiments of the invention relates to rigidizing a surgical tool, for example, in a longitudinal direction for an elongate surgical tool, by coupling the surgical tool to a rigid spine. In some embodiments, the spine includes a one or more joints where one or more of the joints do not compromise axial rigidity of the spine. In an exemplary embodiment, the spine comprises a single joint. In some embodiments, the surgical tool includes a flexible portion. Where, in some embodiments, the flexible portion is alignable with the joint of the spine, so that bending of the spine at the spine joint bends the surgical tool.

In some embodiments, the spine is rigid in an axial direction. In some embodiments, the spine is rigid is a direction of elongation of said spine. In some embodiments, rigidity of the spine enables navigation through resistive tissues and/or through tortuous paths and/or narrow passageways. For example, in laparoscopy and/or arthroscopy, for example, arthroscopic knee joint treatment, e.g. cartilage treatment.

In some embodiments, bending of the spine and thereby the tool enables a wider area and/or range of access angle for treatment with the tool. A potential advantage being a reduction in manipulation of patient tissue and/or a reduction in a number of access channels in patient tissue required for treatment.

A potential benefit of a tool rigidified by a spine is the ability for the spine and tool to have different properties. For example, for the spine to have high stiffness to maneuver to reach surgical site/s e.g. in-between the bones and/or to provide macro positioning within and/or near to resistive tissue using the spine joint while having a tool able to provide finer and/or controlled treatment to tissue e.g. soft tissues like ligaments.

In some embodiments, rigidity of the spine is such that a load applied to the spine in a direction perpendicular to a longitudinal axis of the spine (e.g. at a distal portion of the spine) will cause the spine to bend.

In some embodiments rigidity of the spine is such that, under loads experienced during arthroscopic use the spine at most deflects a small amount, for example, by at most 1°, or at most 5° or at most 10°, or lower or higher or intermediate angles of deflection of the spine body from a straight configuration.

In some embodiments, rigidity of the spine is such that a load of 20 g applied to the spine in a direction perpendicular to a longitudinal axis of the spine (e.g. at a distal end of the spine) causes at most 1°, or at most 5° or at most 10°, or lower or higher or intermediate angles of deflection of the spine body from a straight configuration.

In some embodiments, rigidity of the spine is such that a load of 20 g applied to the spine in a direction perpendicular to a longitudinal axis of the spine (e.g. at a distal end of the spine) causes at most 1°, or at most 5° or at most 10°, or lower or higher or intermediate angles of deflection of an axis of bending of the spine from a straight configuration.

In some embodiments, rigidity of the spine is such that a load of 20 g applied to the spine in a direction perpendicular to a longitudinal axis of the spine (e.g. at a distal end of the spine) causes at most 1°, or at most 5° or at most 10°, or lower or higher or intermediate angles of deflection of the longitudinal axis of the spine relative to the unbent longitudinal axis of the spine.

In some embodiments, rigidity of the spine is such that a load of 20 g applied to the spine in a direction perpendicular to a longitudinal axis of the spine (e.g. at a distal end of the spine) causes at most 1°, or at most 5° or at most 10°, or lower or higher or intermediate angles of deflection of the longitudinal axis of the spine relative to the unbent longitudinal axis of the spine.

In some embodiments, the spine has a small radius of curvature when bent. For example, where, in some embodiments, the radius of curvature differs by less than 50%, or less than 20% or less than 10%, or lower or higher or intermediate percentages, from a depth and/or width of a distal end of the spine. For example, where, in some embodiments, the radius of curvature is less than 10 mm, or less than 5 mm, or less than 2 mm, or less than 1 mm, or lower or higher or intermediate measurements.

In some embodiments, the joint of the spine is short, for example, less than 5 mm, or 4 mm, or 3 mm, or 2 mm, or 1 mm in length along a longitudinal axis of the spine. In some embodiments, the spine joint is a pivot joint. In some embodiments, the spine retains rigidity when bent at the joint.

In some embodiments, the spine joint is positioned at a distal 1-20% of a length of the spine. In some embodiments, the spine joint is positioned at a distal 1-50 mm, or 1-30 mm, or 1-20 mm, of the spine, or lower or higher or intermediate distances or ranges.

In some embodiments, bending of the spine is forceful e.g. enough to overcome resistive forces e.g. of tissue adjacent to the spine.

In some embodiments of the invention a surgical tool is rigidized by coupling the surgical tool to a rigid spine using a sheath. Where, in some embodiments, the surgical tool is disposed within a lumen of the sheath. In some embodiments, a surgical rigid spine coupled to a sheath is herein termed a "working channel device". In some embodiments, the spine is rigid in a direction of elongation of the sheath and/or of the working channel device and/or of a surgical tool. In some embodiments, the sheath and the spine both are elongated and run lengthwise together e.g. to form the working channel device. In some embodiments, the sheath includes a flexible portion which is aligned with the joint of the spine, and, in some embodiments, connection between the sheath and spine is such that bending of the spine bends the flexible portion of the sheath.

In some embodiments, a radius of curvature of the sheath at the sheath flexible portion, when the sheath and spine are bent, is larger than that of the spine, for example, 2-50 times, or 5-20 times, or lower or higher or intermediate ranges or multiples. In some embodiments, this is a potential advantage for a working channel device. Where the device has a spine, the spine having a joint with a small radius of curvature associated with high structural strength, whist the device has a working channel provided by the sheath bent by the spine, with a larger radius of curvature.

In some embodiments, a spine portion is configured to be attached to a plurality of types of sheath, for example, sheaths with different structural and/or material properties. In some embodiments, a spine portion is configured to be attached to sheaths with different size and/or cross section (cross section taken perpendicular to the sheath longitudinal axis). In some embodiments, a spine portion is configured to be attached to tubular sheaths with different diameters. For example, in some embodiments, a kit includes a spine and a plurality of different sheaths and a user selects a sheath for use with the spine e.g. before and/or during a procedure.

In some embodiments, the tool has a longitudinal axis.

In some embodiments, the tool is moveable, for example, one or both of axially (e.g. in a direction parallel to the longitudinal axis of the tool and/or a longitudinal axis of the sheath) and rotationally (e.g. about the tool longitudinal axis and/or the sheath longitudinal axis) with respect to the sheath. Where, in this document, the term "axial movement" refers to movement in a direction parallel to and/or of a longitudinal axis e.g. of the tool and/or sheath and/or spine and/or working channel device system. Where, in this document, the term "rotational movement" refers to rotation about a longitudinal axis e.g. of the tool and/or sheath and/or working channel device system.

A potential benefit being manipulation of the tool during treatment without interfering with patient tissue. A further potential benefit is the ability to sheath the tool within the sheath during positioning of the working channel device e.g. to protect the tool and/or patient tissue from the tool e.g. from damage due to forces associated with positioning of the working channel device.

In some embodiments, the sheath provides support and/or protection to the tool. For example, in some embodiments, the sheath is crush resistant, for example, in one or more directions perpendicular to the sheath longitudinal axis e.g. including flexible portion/s of the sheath.

In some embodiments, axial movement of the tool with respect to the lumen of the sheath enables removal and/or exchange of the tool. For example, during treatment e.g. while the working channel device remains in situ within user tissue. A potential benefit being the ability to access a target region with a plurality of surgical tools, simultaneously and/or sequentially, while retaining the sheath at or near the target region e.g. without need for repeated positioning (e.g. macro-scale positioning of the tool). Further potential benefits being reducing trauma to surrounding tissue from tool positioning and/or maneuver and/or increasing speed of treatment where treatment includes using a plurality of tools (e.g. associated with time saved in introducing and/or positioning each tool).

In some embodiments, the spine is a reusable portion whereas the sheath is disposable. In some embodiments, the system includes a double sheath where an outer cover sheath is configured to cover the spine and an inner sheath is configured (e.g. sized and/or shaped) to cover the tool.

In an exemplary embodiment, one sheath portion is reusable and another sheath portion is disposable. For example, in an exemplary embodiment, an outer sheath is disposable and an inner sheath is reusable. Alternatively both sheath portions, in some embodiments, are reusable or disposable.

In some embodiments, reusable sheath portion/s are sterilizable, In some embodiments, the sterilization is by autoclave.

In some embodiments, the sheath is expandable (e.g. elastic), for example, in a direction perpendicular to the sheath longitudinal axis. Potentially, in some embodiments, enabling insertion of tools where the end effector of the tool has a larger extent than the relaxed width of the sheath. For example, a tool with an end effector with a fixed off-axis (off longitudinal axis of the tool) end effector. Alternatively, or additionally, in some embodiments the sheath is oversized with respect to a body of the tool.

An aspect of some embodiments of the invention relates to a working channel device system where actuation and/or locking of one or more movements of the sheath and/or of the tool is controlled at a proximal end of the system e.g. at a handle region of the system. In some embodiments, control is of one or more of; actuation of bending of the working channel, actuation of the surgical tool, and movement (e.g. axial and/or rotational) of the tool with respect to the channel. In some embodiments, locking is of one or more of; actuation of the spine, actuation of the tool, and movement of the tool with respect to the spine.

Activation of an end effector (e.g. end effector, in some embodiments, includes actuating the end effector (e.g. needle/s, suture passer/s, grasper/s, cutter/s and/or electronic end effector/s) using a flexible wire mechanism such as disclosed in pending patent application USP62/279,817, the disclosure of which is hereby incorporated by reference in its entirety.

In an exemplary embodiment, control is at a single handle region of the system. A potential benefit being ease of use. In some embodiments, a user is able to control more than one of the control features at the channel using a single hand grasping the handle. In some embodiments, the working channel device has a small cross sectional extent (e.g. extent in a direction perpendicular to a longitudinal axis of the device). For example, an average cross sectional area of a distal portion of the device (e.g. at a distal 10% of the device) is 1-20 $mm^2$ or 1-10 $mm^2$, or 1-5 $mm^2$, or lower or higher or intermediate ranges or areas.

In some embodiments, the spine has a small cross sectional extent (e.g. extent in a direction perpendicular to a longitudinal axis of the spine). For example, an average cross sectional area of a distal portion of the device (e.g. at a distal 10% of the device) is 1-10 $mm^2$ or 1-5 $mm^2$, or 1-2 $mm^2$, or lower or higher or intermediate ranges or areas.

A potential benefit of a small cross section device is the ability to perform treatment with small incisions associated with potentially one or more of; less scarring, reduced trauma to the patient and faster healing time.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Working Channel Device

Figure 1A:
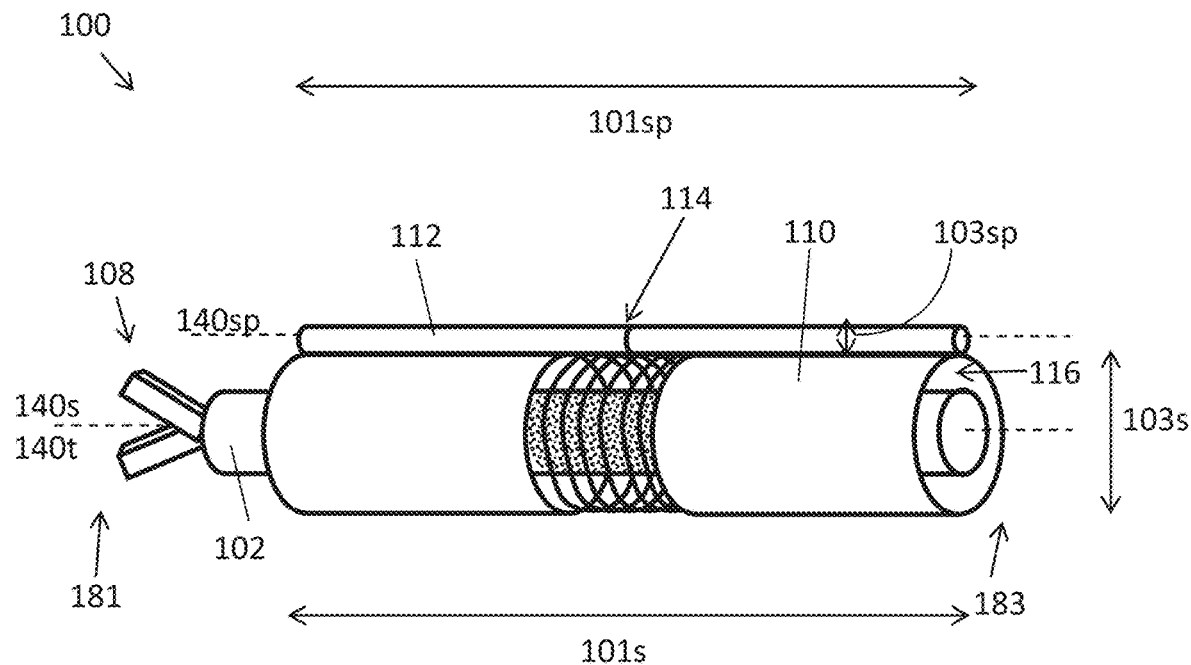
FIG. 1A is a simplified schematic of a tool disposed within a lumen of a working channel, according to some embodiments of the invention.

FIG. 1A is a simplified schematic of a working channel device system 100, according to some embodiments of the invention.

In some embodiments, working channel device system 100 includes a working channel device 106 and a tool 102. Where, in some embodiments, tool 102 is disposed within a lumen 116 of sheath 110. In some embodiments, tool 102 includes an end effector 108.

In some embodiments, working channel device 106 includes a sheath 110 coupled to a spine 112. Where, in some embodiments, spine 112 includes a joint 114.

In some embodiments, spine 112 is disposed external to sheath 110. In some embodiments, spine 112 reinforces sheath 110 in a direction parallel to a longitudinal axis 140$s$ of lumen 116 of sheath 110.

In some embodiments, sheath 110 is elongated, where, for example, a length 101$s$ of sheath 110 is larger than a width 103$s$ of sheath 110. In some embodiments, length 101$s$ is 2-500 times, or 20-300 times, or 50-200 times, longer than width 103$s$, or lower or higher or intermediate multiples or ranges. Where, when sheath 110 has constant circular cross section, width 103$s$ is a diameter of sheath 110. If sheath 110 has non-circular cross section, for one or more longitudinal portion of sheath 110 and/or has changing cross section shape and/or dimensions, in some embodiments, width 103$s$ of sheath 110 is calculated as an average dimension of sheath 110 perpendicular to a longitudinal axis 105$s$ of sheath 110.

In some embodiments, spine 112 is elongated, where, for example, a length 101$sp$ of spine 112 is larger than a width 103$sp$ of spine 112. In some embodiments, length 101$sp$ is 2-500 times, or 50-400 times, or 100-300 times larger than width 103$sp$ or lower or higher or intermediate multiples or ranges. Where width 103$sp$ of spine 112 is, in some embodiments, calculated as an average extent of spine 112 perpendicular to a longitudinal axis 140$sp$ of spine 112.

In some embodiments, the term longitudinal axis refers to a central longitudinal axis of a component. For example, in a case where the component is tubular with circular cross section, the longitudinal axis runs through a center-point of the circular cross section. For example, as illustrated by sheath longitudinal axis 105s and spine longitudinal axis 140sp in FIG. 1B.

In some embodiments, spine 112 and sheath 110 are connected such that their longitudinal axes 103s, 103sp, are aligned, e.g. are parallel or at an angle of at most have 10°, or 5°, or 1°.

In some embodiments, spine 112 and sheath 110 are connected overlapping, such that at least a portion of sheath 110 overlaps with spine 112 e.g. at least a distal portion of sheath 110, e.g. at least 5%, or at least 10%, or at least 20% of sheath length 101s.

In some embodiments, tool 102 is elongated, where, for example, a length 101sp of tool 102 is larger than a width 103t of tool 102. In some embodiments, length 101t is 2-500 times, or 50-400 times, or 100-300 times than width 103t, or lower or higher or intermediate multiples or ranges. Where width 103t of tool 102 is, in some embodiments, calculated as an average extent of tool 102 perpendicular to a longitudinal axis 105t of spine 102. In some embodiments, tool 102 dimensions are of tool body 120 e.g. excluding tool end effector 108.

In some embodiments, working channel device system 100 includes a distal end 181 and a proximal end 183. In this document, relative position of portions of the system are referred to using the terms "distal" and "proximal" to indicate relative position along a longitudinal axis of the system and/or of a part of the system, for example, surgical tool longitudinal axis 105t, a sheath longitudinal axis 105s, spine longitudinal axis 140sp.

In some embodiments, a user, when using working channel device 100 grasps a proximal portion 124 of working channel device 106. In some embodiments, one or more mechanisms for control of tool 102 and/or working channel device 106 (e.g. bending of spine 112) are operated by the user grasping proximal portion 124 and/or are located at least in part in proximal portion 124.

Figure 1B:
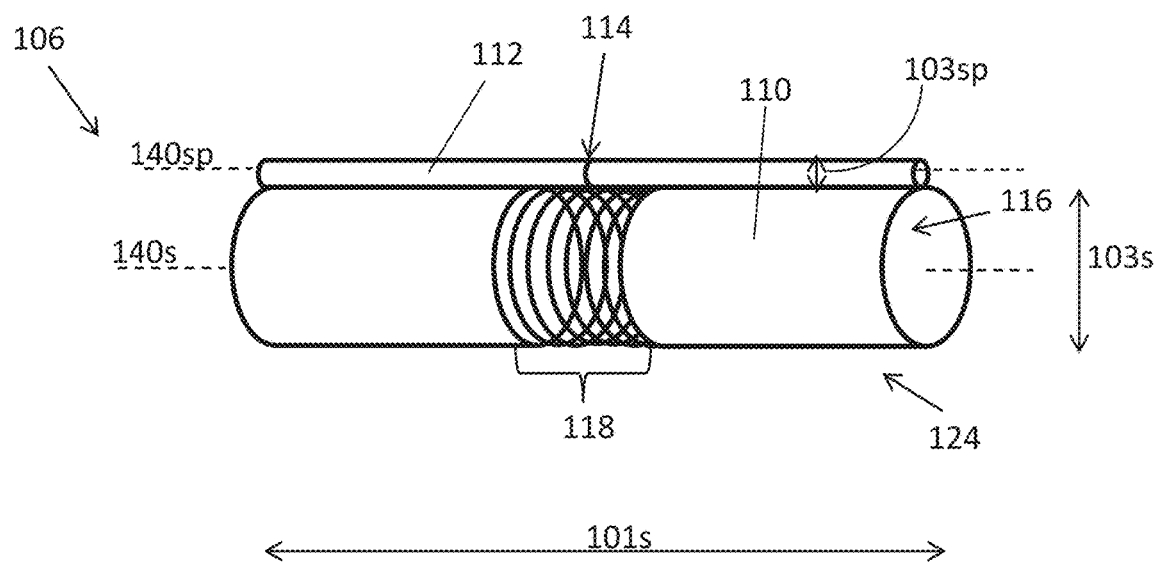
FIG. 1B is a simplified schematic of a working channel, according to some embodiments of the invention.

FIG. 1B is a simplified schematic of a working channel device 106, according to some embodiments of the invention.

In some embodiments, working channel device 106 of FIG. 1B is the working channel device of FIG. 1A. In some embodiments, working channel device 106 includes a sheath 110 and a spine 112. In some embodiments spine 112 includes a joint 114. In some embodiments, sheath 110 includes a lumen 116. In some embodiments, sheath 110 includes a flexible portion 118. In some embodiments, spine 112 is coupled to sheath 110 such that joint 114 is positioned such that the flexible portion 118 overlaps with joint 114.

In some embodiments, sheath 110 is made of low durometer material, for example, polyurethane and/or plastic where in some embodiments, the material is reinforced e.g. by braiding and/or coiling.

In some embodiments, one or more portion of sheath 110 is constructed of a solid sheet of material, which, in some embodiments, is tubular. Additionally or alternatively, in some embodiments, one or more portions of sheath 110 includes one or more features as described regarding FIGS. 22A-D FIG. 1C is a simplified schematic of a tool 102, according to some embodiments of the invention.

Figure 1C:
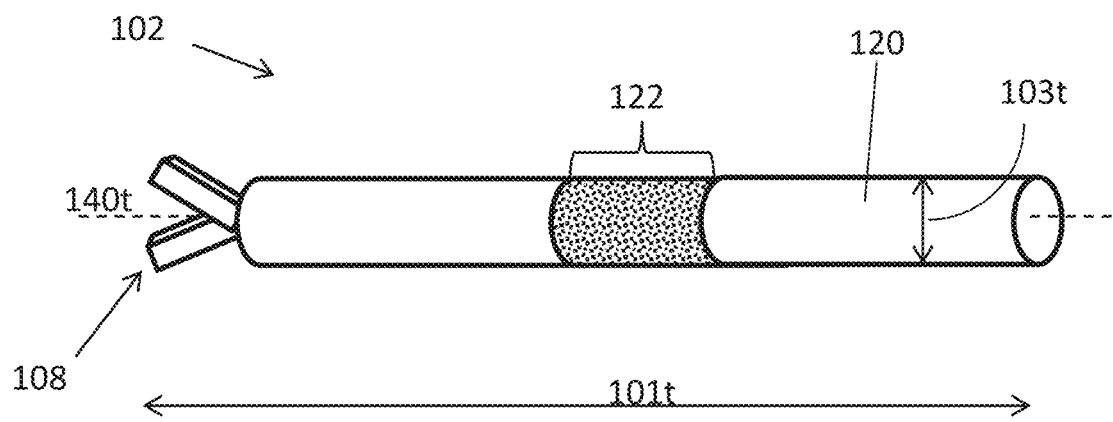
FIG. 1C is a simplified schematic of a tool, according to some embodiments of the invention.

In some embodiments, tool 102 of FIG. 1C is the tool 102 of FIG. 1A. In some embodiments, tool 102 includes a tool body 120 to which an end effector 108 is coupled. In some embodiments, tool 102 includes a flexible portion 122. For example, in some embodiments, at least portion 122 of tool body 120 along a longitudinal axis 140t of tool body 120 is flexible. In some embodiments, at least 1%, or at least 2%, or at least 5%, or at least 10%, or of a length of tool body 120 is flexible. In some embodiments, an entire length of tool 102 is flexible.

Exemplary end effectors 108 include, in some embodiments, needle/s, suture passer/s, grasper/s, cutter/s, imager/s (e.g. endoscopic camera).

In some embodiments, end effector 108 is fixedly attached to a distal portion (e.g. distal end) of tool body 120. In some embodiments, tool body 120 is compatible (e.g. attachable to and/or detachable from) with more than one type of end effector.

Figure 2:
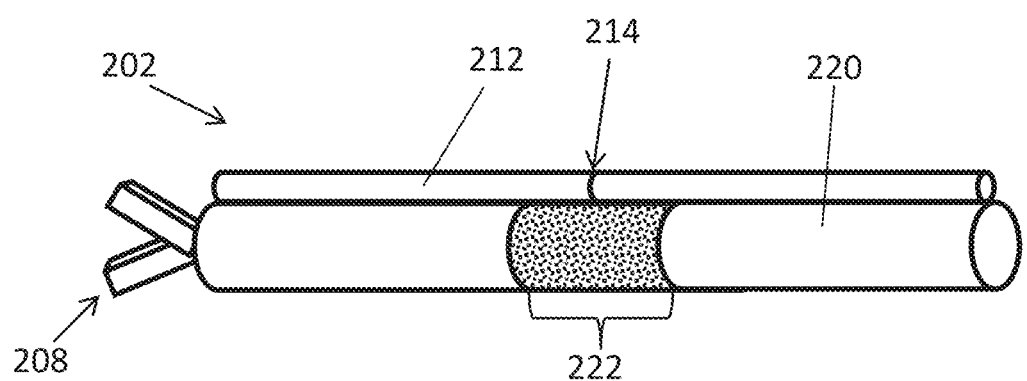
FIG. 2 is a simplified schematic of a tool 202, according to some embodiments of the invention.

FIG. 2 is a simplified schematic of a tool 202, according to some embodiments of the invention. In some embodiments, tool 202 includes a flexible portion 222 and is directly connected to a spine 212 including a joint 214 (flexible portion 222 and joint 214 being aligned) tool 202 being rigidified by spine 212. Optionally, in some embodiments, tool 202 is protected by a cover, not illustrated in FIG. 2.

Exemplary Method

Figure 3:
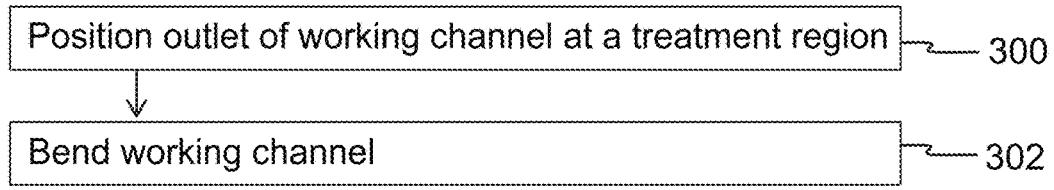
FIG. 3 is a method of treatment, according to some embodiments of the invention.

FIG. 3 is a method of treatment, according to some embodiments of the invention.

At 300, in some embodiments, an outlet of a working channel device reinforced by a spine (e.g. working channel device 106 FIGS. 1A-B, e.g. working channel device 506 FIG. 5B and FIG. 5D) is positioned at a treatment region.

In some embodiments, positioning includes inserting the working channel device through a channel in a subject's tissue. The channel, in some embodiments, extending to the treatment region e.g. from outside the patient's external skin surface through tissue to the treatment region. In some embodiments, positioning includes piercing the subject's tissue, e.g. to generate e.g. at least partially, a channel in the subject's tissue.

In some embodiments, at least a portion of positioning is of the working channel device and a tool is inserted through a lumen of a sheath of the working channel device afterwards.

In some embodiments, at least a portion of positioning is of a working channel system including the working channel device with a tool positioned within a lumen of a sheath of the working channel device.

In some embodiments, the treatment region is within a joint, for example, within a knee joint.

At 302, in some embodiments, a spine of the working channel device is bent, for example, within the treatment region. In some embodiments, bending of the spine bends the tool e.g. the spine bends the working channel and thereby the tool.

Figure 4A:
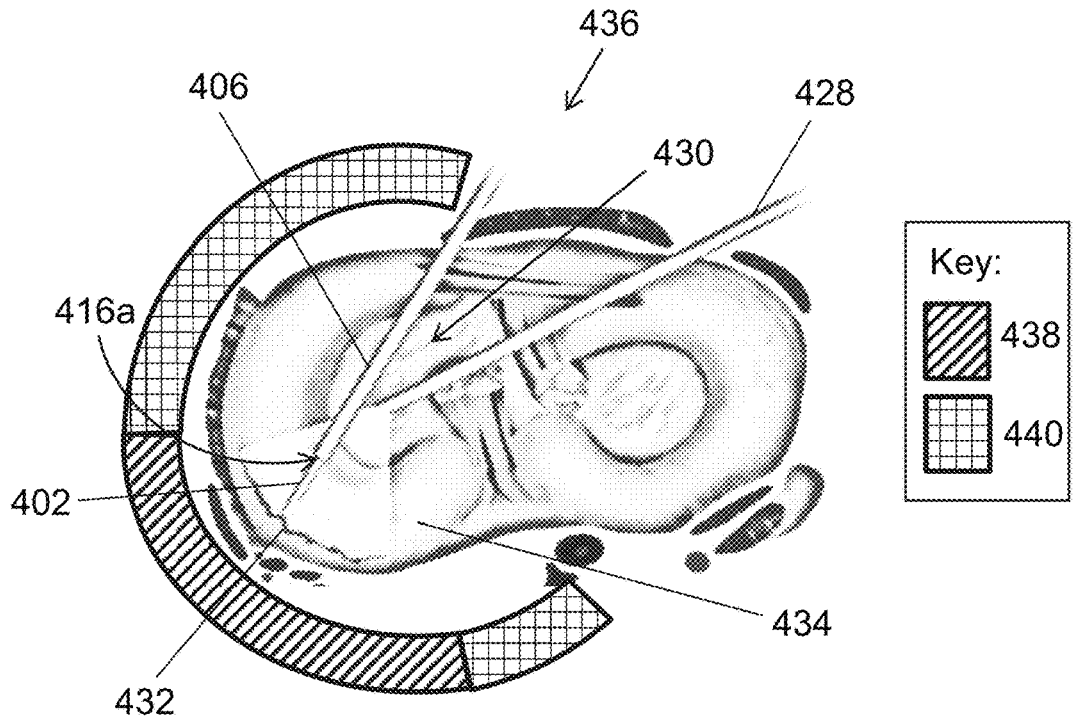
FIG. 4A is a simplified schematic of a working channel device and patient anatomy, according to some embodiments of the invention.

FIG. 4A is a simplified schematic of a working channel device 406 and patient anatomy, according to some embodiments of the invention.

In some embodiments, FIG. 4A illustrates working channel device 406 positioned such that an opening 416a of a lumen of working channel device 406 is within a joint 436 (e.g. knee joint) of a patient. In some embodiments, a tool 402 protrudes from a lumen of working channel device 406. In some embodiments, tool 402 is used to treat and/or diagnose an injury in patient tissue e.g. a cartilage injury 432. In some embodiments, cartilage to be treated is approached by tool 402 from a region 430 at least partially enclosed by cartilage. In some embodiments, an additional tool 428 (e.g. a camera) is used during treatment with working channel device 406. In some embodiments, additional tool 428 is inserted through a different channel in patient tissue.

A potential benefit of a bendable working channel device is increased range of access, for example, of a tool inserted through a lumen of working channel device 406. For example, as illustrated in FIG. 4A where a first region 438 of patient tissue (e.g. cartilage region) is accessible by tool 402 if working channel 406 remains in a straight configuration and a second region 440 of patient tissue is accessible by tool 402 e.g. if working channel device 406 bends tool 402.

Figure 4B:
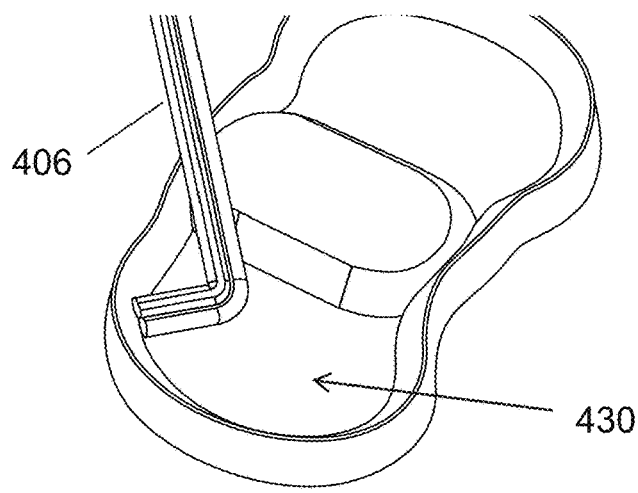
FIG. 4B is a simplified schematic of a working channel device and patient anatomy, according to some embodiments of the invention.

FIG. 4B is a simplified schematic of a working channel device 406 and patient anatomy 430, according to some embodiments of the invention.

In FIG. 4B working channel device 406 is illustrated in a bent configuration.

Exemplary Device

Figure 5A:
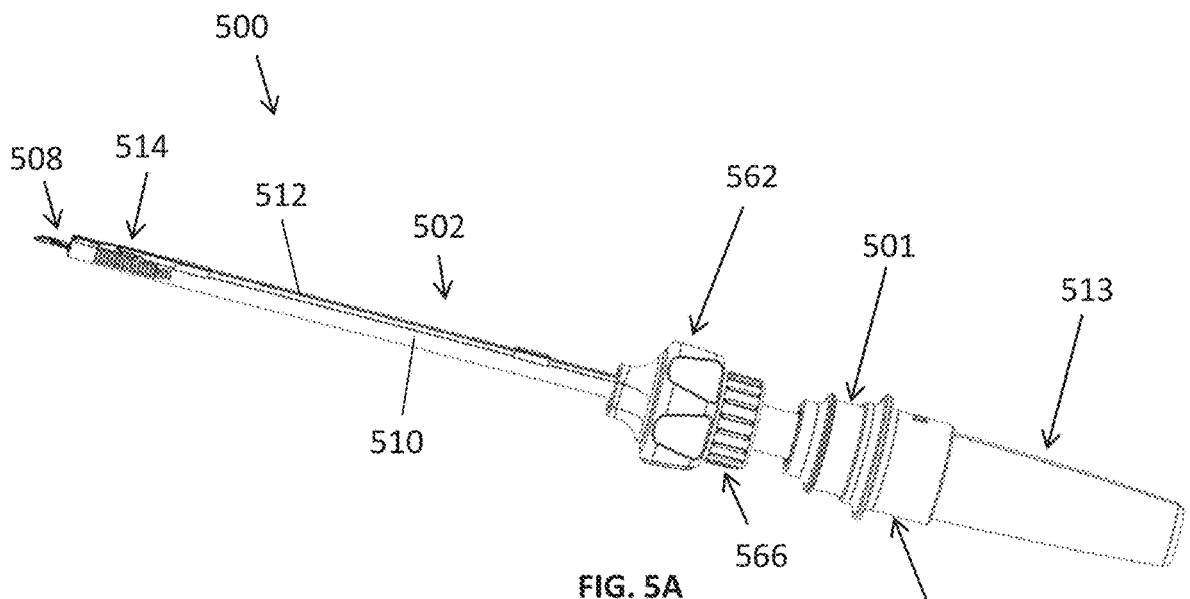
FIG. 5A is a simplified schematic of a working channel device system, according to some embodiments of the invention.

FIG. 5A is a simplified schematic of a working channel device system 500, according to some embodiments of the invention.

Where, in some embodiments, system 500 includes a tool disposed within a lumen of a working channel device 502.

Figure 5B:
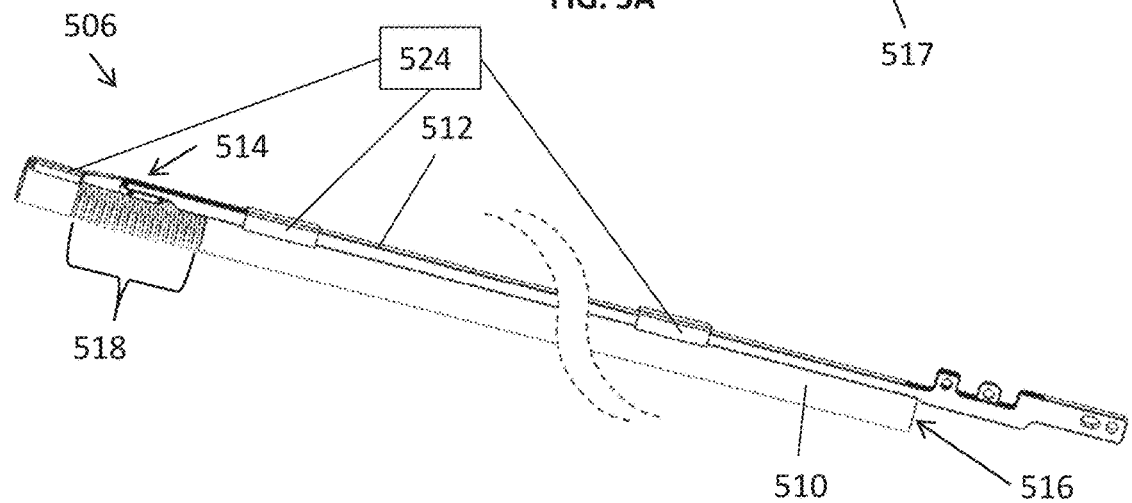
FIG. 5B is a simplified schematic of a working channel, according to some embodiments of the invention.

FIG. 5B is a simplified schematic of a working channel device 506, according to some embodiments of the invention.

Figure 5C:
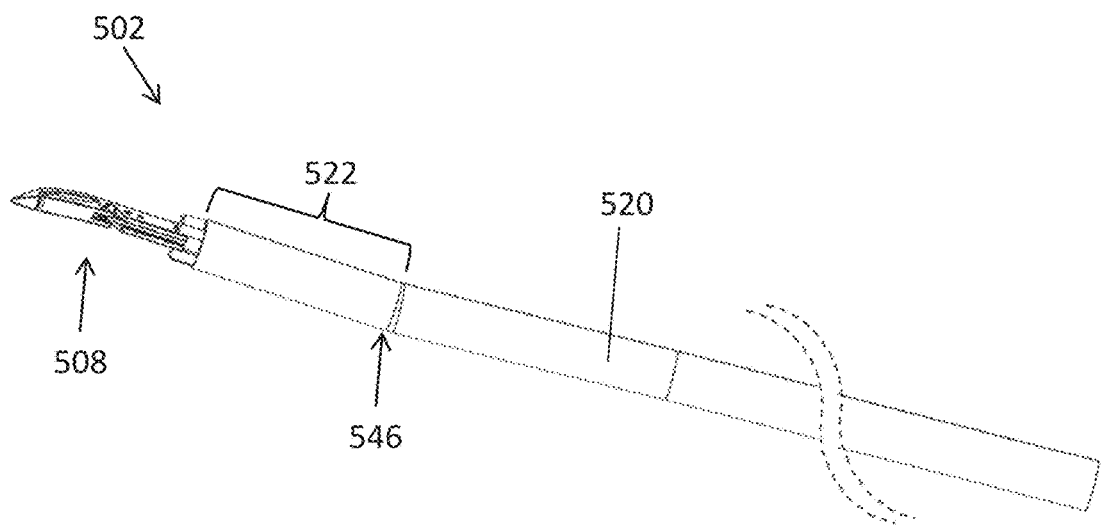
FIG. 5C is a simplified schematic of a tool, according to some embodiments of the invention.

FIG. 5C is a simplified schematic of a tool 502, according to some embodiments of the invention.

In some embodiments, working channel device system 500 includes a tool 502 which is disposed within a lumen 504 of a working channel device 506.

In some embodiments, tool 502 includes an end effector 508.

In some embodiments, working channel device 506 includes a sheath 510 coupled to a spine 512. Where, in some embodiments, spine 512 includes a joint 514.

In some embodiments, spine 512 is external to working channel 506.

FIG. 5B is a simplified schematic of a working channel device 506, according to some embodiments of the invention.

In some embodiments, working channel device 506 of FIG. 5B is working channel device 506 of FIG. 5A.

In some embodiments, working channel device 506 includes a sheath 510 and a spine 512. In some embodiments spine 512 includes a joint 514. In some embodiments, sheath 510 includes a lumen 516.

In some embodiments, sheath 510 includes a flexible portion 518. In some embodiments, a length (e.g. in the longitudinal direction) of flexible portion 518 is 1-20%, or 1-10%, or 1-5% of a length of sheath 510. In some embodiments, flexible portion 518 is 1-50 mm, or 1-20 mm, or 1-10 mm, or lower or higher or intermediate lengths or ranges. In some embodiments, an average cross-sectional extent (e.g. at least of a distal 10% or 20% of sheath 510) is 1-20 mm, or 1-10 mm, or 3-10 mm, or lower or higher or intermediate measurements or ranges. In some embodiments, a majority or all of sheath 510 is flexible.

In some embodiments, a distal end of sheath 510 is rigid. In some embodiments, a proximal portion of sheath 510 is rigid. For example, two rigid portions being connected by flexible portion 518. In some embodiments, a distal 1-5% of a length of sheath 510 is rigid and/or a proximal 20-97% of sheath 510 length is rigid.

In some embodiments, spine 512 is coupled to sheath 510 such that joint 514 is positioned within a longitudinal extent of flexible portion 518.

In some embodiments, spine 512 is attached to sheath 510 by one or more connectors 524. Where exemplary connectors are described, for example, in FIGS. 23A-B and associated text.

In some embodiments, one or more portions of sheath 510 are expandable (e.g. elastically expandable) in one or more directions perpendicular to the longitudinal axis of sheath 510. For example, in some embodiments, at least a portion of sheath 510 is constructed of braid which allows, for example, radial expansion (e.g. compensated by longitudinal contraction). Expansion, for example, enabling passage through sheath 510 of a tool with a portion (e.g. end effector) of larger extent than a relaxed diameter of sheath 510. For example, a tool with a fixed off-axis (e.g. off-axis of a longitudinal axis 503*t* of tool body 520) end effector. For example, a tool bent at a joint of the tool.

In some embodiments, at least a portion of the length of sheath 510 is crush resistant, for example in a radial direction. In some embodiments, sheath 510 is constructed of material which provides radial strength (e.g. crush resistance). Exemplary materials for construction of sheath 510 include metal, polymer, reinforced spring, braid, low durometer tube, PVC, coiled spring, spiral cross section tube, spiral tube or any other material that provides radial reinforcement.

In some embodiments, sheath 510 is continuous, for example, formed of one piece of material.

In some embodiments, sheath 510 is constructed from more than one part where, in some embodiments, at least one of the parts includes different material and/or mechanical characteristics than other portion/s.

In some embodiments, sheath 510 includes two rigid tubes connected by a flexible tubular portion e.g. flexible portion 518 being tubular and/or including one or more of; coupled links, a coil, a mesh. In some embodiments, flexible portion 518 is elastically bendable. In some embodiments, flexible portion is ductile 518. In some embodiments, sheath 510 is a closed tubular structure. Alternatively, in some embodiments, one or more portions of sheath 510 has an opening. Where the opening/s in some embodiments, includes one or more slit and/or aperture and/or slot and/or bore.

In some embodiments, tool 502 of FIG. 5C is the tool of FIG. 5A. In some embodiments, tool 502 includes a body 520 to which an end effector 508 is coupled. In some embodiments, tool body 520 includes a flexible portion 522. For example, in some embodiments, at least a longitudinal portion of tool body 520 is flexible 522. Alternatively or additionally to having a flexible portion, in some embodiments, tool body 520 includes one or more joints 546.

Figure 5D:
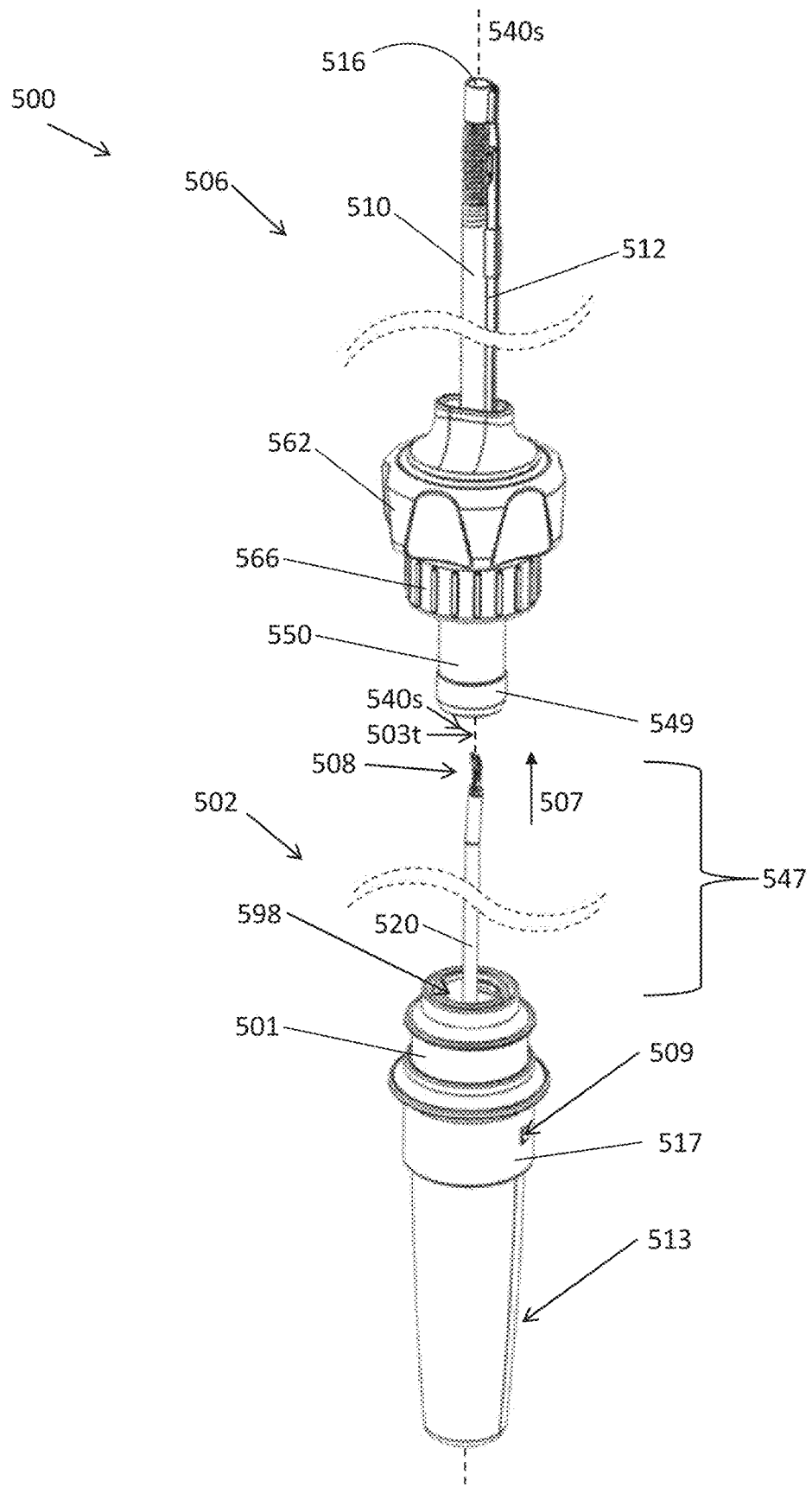
FIG. 5D is a simplified schematic of a system, according to some embodiments of the invention.

FIG. 5D is a simplified schematic of a system 500, according to some embodiments of the invention.

In some embodiments, system 500 includes a working channel device 506 and a tool 502. Where a distal portion 547 of tool 502, in some embodiments, is slidably inserted into a lumen 516 of a sheath 510 of working channel device 506.

In some embodiments, working channel device 506 includes actuator/s for bending 562 and/or locking 566 of spine actuation, which, in some embodiments, are disposed at a proximal portion of working channel device 506.

In some embodiments, working channel device system 500 includes actuator/s for actuation of tool 502 and/or for locking of axial movement of tool 502 with respect to sheath 510. Where, for example, as described in more detail regarding FIGS. 11A-F, in some embodiments, working channel device system 500 includes one or more of a spine actuation knob 562 (1162 FIGS. 11A-F), a spine bending locking knob 566 (1155 FIGS. 11A-F), an axial movement lock portion 501 (1101 FIGS. 11A-F).

In some embodiments, when tool 502 is coupled to working channel device 506 by insertion of distal portion 547 of 502 tool into lumen 516 of sheath 510, actuator/s (e.g. one or more of actuators 562, 566, 501, 517) occupy a proximal portion of the working channel device system 500. Where, in some embodiments, one or more of actuators 562, 566, 501, 517 form a single handle region (e.g. handle region 699 FIG. 6, handle region 799 FIGS. 7A-B). For example, where actuation and/or locking of movement of one or more parts of working channel device system 500 is controlled e.g. by a user grasping the handle region (e.g. handle region 699 FIG. 6, handle region 799 FIGS. 7A-B) e.g. single-handedly.

In some embodiments, working channel device 506 and tool 502 are coupled such that tool 502 does not easily decouple from working channel device 506. For example, tool 502 and working channel device 506 do not decouple under the force of gravity e.g. when tool 502 is under working channel device 506.

In some embodiments, working channel device 506 and tool 502 are coupled by elastic portion/s 598 which elastically deflect when working channel device base portion 550 is moved proximally past elastic portion/s 598 (or elastic portion/s 598 are moved distally onto base portion 550). (Elastic portion/s 598 in some embodiments, are part of a handle 513 of tool 502 e.g. elastic portions 1298a, 1298b FIGS. 12D,12F and 12G.)

In some embodiments, one or more protruding portions 549 on base portion 550 prevent decoupling. Where, in some embodiments, protruding portion 549 protrudes radially outwardly.

In an exemplary embodiment, protruding portion 549 is a single annular portion which has a larger radial extent than the rest of a proximal portion of base portion 550. For example, in some embodiments, protruding portion 549 is a nut which is screwed onto base portion 550.

Alternatively or additionally, in some embodiments, there is more than one protruding portion which prevents decoupling. For example, a plurality of radially protruding portions disposed on base portion 550.

Figure 6:
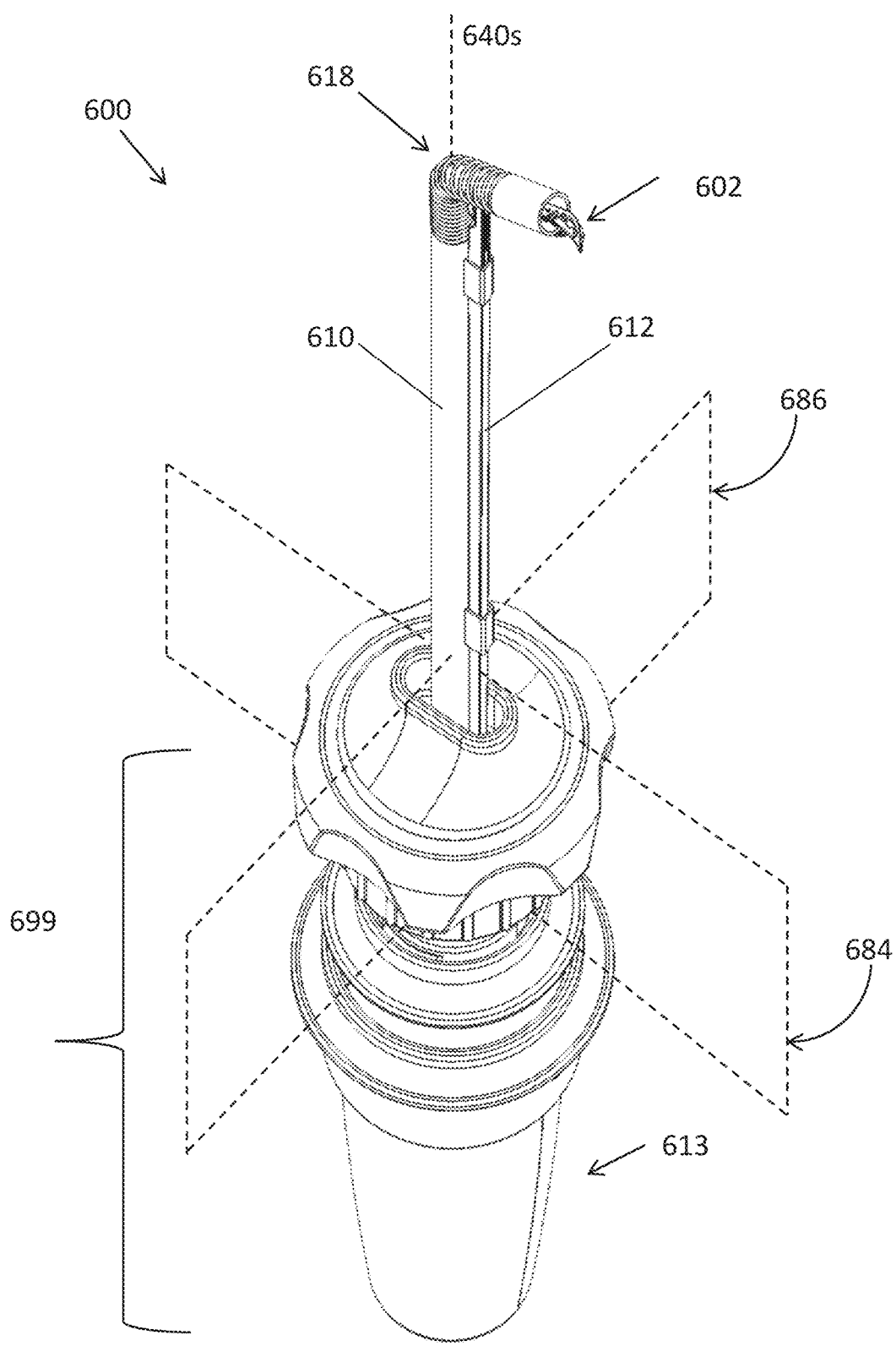
FIG. 6 is a simplified schematic of a device according to some embodiments of the invention.

FIG. 6 is a simplified schematic of a device 600 according to some embodiments of the invention.

In some embodiments, a spine 612 bends to bend a flexible portion 618 of a sheath 610, in some embodiments, thereby bending a tool 602. Where bending, for example, is with respect to a sheath body longitudinal axis 640s.

FIGS. 7A-B are simplified schematics of a device 700 according to some embodiments of the invention.

Dashed lines between FIGS. 7A-B are to illustrate relative movement of parts between the configurations illustrated in FIG. 7A and FIG. 7B.

In some embodiments, a working channel device system 700 includes a tool 702 which is axially moveable with respect to a sheath 710. For example, to extend and/or retract tool 702 with respect to sheath 710. In some embodiments, tool 702 is retractable to be fully axially enclosed by sheath.

In some embodiments, tool is extendable distally, outwards from a distal opening of sheath 710 by up to 30 mm, or by up to 20 mm, or by up to 10 mm, or by up to about 12 mm, or by lower or higher or intermediate distances.

In some embodiments, arrow 742 illustrates movement of sheath 710 between the configuration illustrated in FIG. 7A to the configuration illustrated in FIG. 7B.

In some embodiments, sheathing and/or extension of tool 702 is by axial movement of sheath 710 (e.g. as illustrated in FIGS. 7A-B). Alternatively or alternatively, in some embodiments, it is by axial movement of tool 702.

In an exemplary embodiment, sheath 710 is fixed axially, for example, a proximal portion of sheath 710 is fixed axially e.g. to a capping portion 752. In some embodiments, a user moves capping portion 752 axially, to sheathe and/or retract tool 702.

In some embodiments, tool 702, is axially moveable with respect to capping portion 752 (as well as remaining axially moveable with respect to sheath 710). In some embodiments, for example, tool 702 extends proximally passing through a channel within capping portion 752. In some embodiments, capping portion 752 is moved to sheathe/extend tool 702 from sheath 710 e.g. as illustrated in FIG. 7A and FIG. B by movement of capping portion 752 between FIG. 7A and FIG. 7B.

Exemplary details of geometrical interaction between sheath 710, tool 702 and capping portion 752 are illustrated, for example, by sheath 1110, tool body 1120, and capping portion 1152 of FIG. 11F.

In some embodiments, tool 702 has a longitudinal axis 705t and the tool body 720 is rotatable e.g. around this axis within sheath 712. In some embodiments, tool 702 is rotatable when sheath 712 is bent at sheath flexible section 718 (and/or when sheath 712 is in a straight configuration).

In some embodiments, sheathing of tool 702 inside sheath 712 is actuated by rotation of a knob where the rotational movement is transferred to relative axial movement between tool 702 and sheath 712.

FIGS. 7C-D are simplified schematics of a distal end of a device, according to some embodiments of the invention.

FIGS. 7C-D, in some embodiments, illustrate axial movement, in some embodiments, of a tool 702 with respect to a sheath 710, when sheath 710 and tool 702 are in a bent configuration. In some embodiments, tool 702 is at least partially disposed within a lumen 704 of sheath 710.

FIGS. 8A-B are simplified schematics of a distal end of a device 800, according to some embodiments of the invention.

FIGS. 8A-B, in some embodiments, illustrate rotation of a tool 802 within a lumen 816 of a sheath 810 of a working channel device 800. Where rotation is, for example, around a longitudinal axis 840 of tool body 820 and/or around a longitudinal axis of lumen 816 of sheath 840.

In some embodiments, tool 602 fits closely within lumen 816 of sheath 810. For example, with at most 3 mm, or 2 mm, or 1 mm, or 0.5 mm of space (e.g. in total) along a line connecting opposite inner walls (the line e.g. passing through a center point of sheath 810) of sheath 810 between the tool body and the sheath inner walls. For example, with at most 3 mm, or 2 mm, or 1 mm, or 0.5 mm difference between the tool body outer diameter and the sheath inner diameter. In some embodiments, there is sufficient space between tool 602 and the inner walls of sheath 610 such that tool 602 bends within sheath 610 and/or as unsheathing e.g. as illustrated in FIG. 8B. Alternatively or additionally, FIG. 8B illustrates embodiments where tool 602 includes one or more articulation where bending at the articulation is not actuated by bending of sheath 610. For example, tool 602, in some embodiments, has a shape memory. For example, tool 602 elastically moving to a bent configuration upon unsheathing. For example, tool 602 having a fixed angle.

Exemplary Detailed Method

FIG. 9 is a detailed method of treatment, according to some embodiments of the invention.

At 900, optionally, in some embodiments, an imager (e.g. endoscopic camera) is positioned, for example, at a treatment site, for example, by being inserted through a channel in patient tissue.

At 902, in some embodiments, a working channel device is positioned at a treatment region. Where, in some embodiments, an outlet of a sheath of the working channel device is positioned at a treatment region (which outlet, in some embodiments, is at a distal end of the sheath).

In some embodiments, a user positions the working channel using visual feedback e.g. provided by an imager (e.g. the imager positioned at step 900 and/or external imaging e.g. ultrasound).

At 904, in some embodiments, the tool is positioned, for example, by one or more of steps 906-910:

At 906, in some embodiments, an axial position of a tool is changed with respect to the lumen of the sheath of the working channel device. For example, in some embodiments, a tool within the sheath is extended distally out of the outlet of the sheath. For example, in some embodiments, a tool is inserted into the sheath.

At 908, in some embodiments, a spine of the working channel device is bent, for example, to position the tool (e.g. an end effector of the tool) at a position which is off-axis of a longitudinal axis of the spine and/or sheath lumen. Optionally, in some embodiments, once the spine is bent to a desired angle, spine bending is locked.

At 910, in some embodiments, the tool is rotated, for example to change an orientation of the end effector. Where rotation is, for example, around a longitudinal axis of the tool (e.g. tool body) and/or around a longitudinal axis of the lumen of the sheath.

At 912, in some embodiments, tissue is treated by the tool. Where, treatment, in some embodiments, includes one or more of; cutting, abrading, suturing, drilling, shaving, grasping, ablating, penetrating (e.g. penetrating soft tissue), and positioning anchoring element/s. In some embodiments, treatment includes removing tissue. In some embodiments, treatment includes positioning an object and/or attaching an object to patient tissue e.g. a prosthetic (e.g. artificial cartilage). In an exemplary embodiment, treatment is a meniscus procedure.

At 914, in some embodiments, one or more objects are delivered to the treatment area e.g. through the sheath lumen. For example, one or more of suture thread, anchor elements, artificial cartilage and irrigation. For example, in some embodiments, one or more additional tools are inserted through the sheath. For example, where additional tool/s are inserted in addition to a first tool. For example, where additional tool/s are inserted after withdrawal of a first tool.

At 916, optionally, in some embodiments, a tool is exchanged. Exchange, for example, including removing a first tool and inserting a second tool. Where, in some embodiments, the second tool is positioned (e.g. in one or more of steps 906-910). In some embodiments, bending of the working channel is changed, for example, reduced, for example, temporarily, for axial movement of tool/s e.g. insertion and/or withdrawal of tool/s. In some embodiments, bending of the spine is locked (e.g. as described in step 908) before tool exchange.

At 918, in some embodiments, the working channel device is removed e.g. withdrawn from the patient's tissue.

At 920, in some embodiments, access wound/s are closed (e.g. with stitches and/or surgical glue) and/or dressed.

In some embodiments, the working channel device system is used in conjunction with other tools. For example, one or more standard laparoscopic and/or arthroscopic tool. In some embodiments, treatment is performed using more than one working channel device system, for example, a first system at a first incision and a second system at a second incision.

Exemplary Spine

FIGS. 10A-E are simplified schematics of spine portions 1012, according to some embodiments of the invention.

In some embodiments, bending of a spine 1012 of a working channel device, at a spine joint 1014, is actuated by relative movement of a first spine rod 1072 and a second spine rod 1074. For example, axial relative movement between first and second spine rods 1072, 1074.

In some embodiments, bending of spine 1012 is by a bending portion 1078 of spine 1012 changing orientation with respect to one or more other portions of spine 1012 e.g. first spine rod 1072 and/or second spine rod 1074.

Figure 10A:
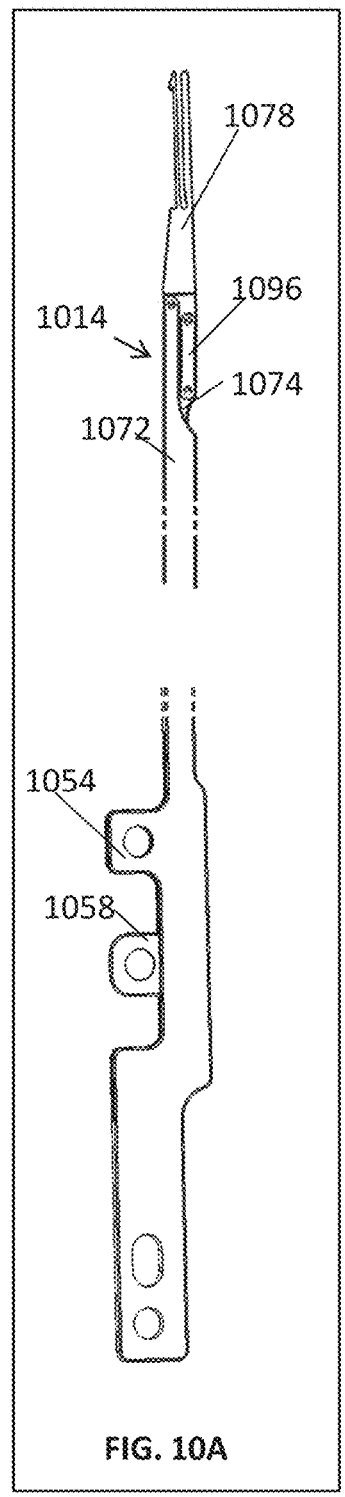
Figure 10B:
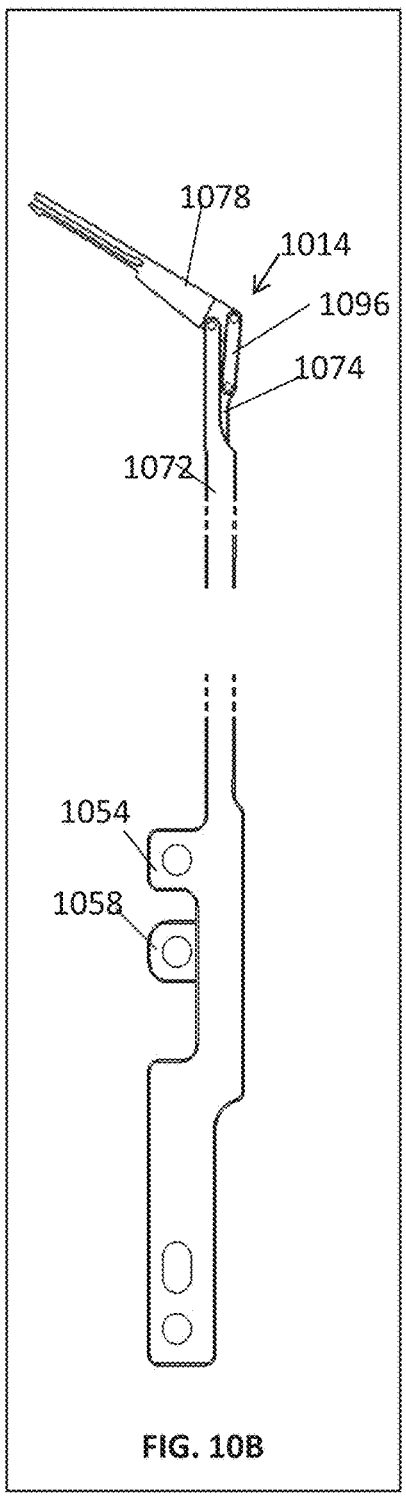
Figure 10C:
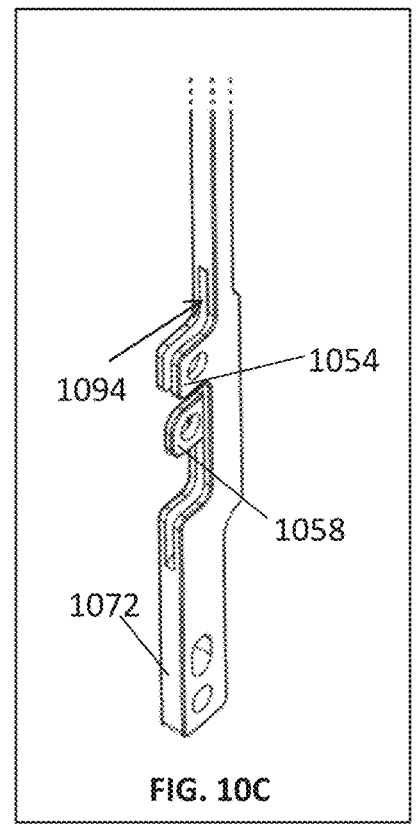
Figure 10D:
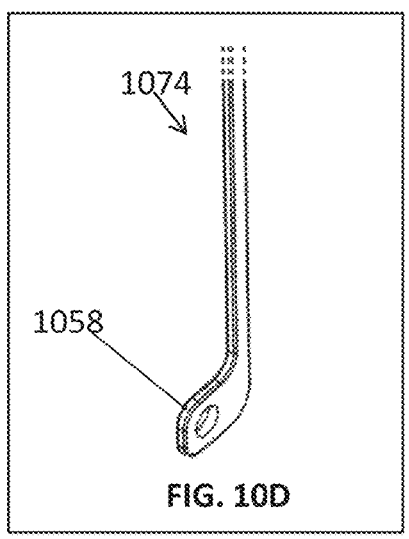

In some embodiments, second spine rod 1074 is at least partially enclosed within first spine rod 1072 (e.g. within a lumen 1094 of first spine rod 1072, see, for example, FIG. 10C).

Figure 10E:
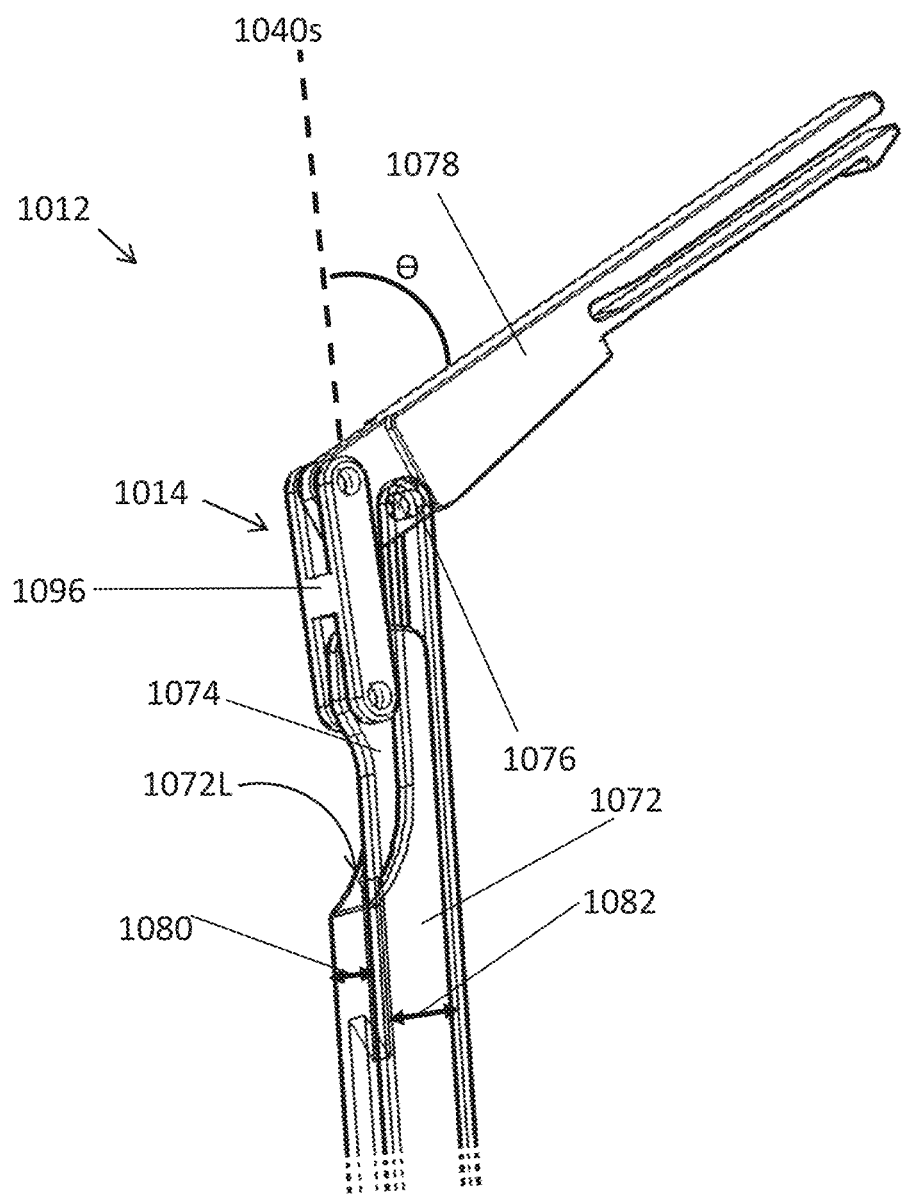

Referring now to FIG. 10E, in some embodiments, spine joint 1014 includes a pivot 1076 where bending of spine 1012, in some embodiments, includes pivoting of bending portion 1078 about pivot 1076.

In some embodiments, pivoting of bending portion 1078 is actuated by push/pull movement of second spine rod 1074. For example, in an exemplary embodiment, second spine rod 1074 is pushed longitudinally to bend spine 1012, the "pushing" force being applied in a distal direction. In some embodiments, second spine rod 1074 is "pulled" longitudinally to straighten spine 1012.

In some embodiments, bending portion 1078 is tapered, for example, tapering distally e.g. in one or more directions. In some embodiments, tapering of bending portion 1078 reduces an extent of a distal end of spine 1012 and/or of working channel device (e.g. working channel device 106 FIGS. 1A-B, e.g. working channel device 506 FIG. 5B and FIG. 5D). For example, tapering of bending portion 1078, reducing an extent of bending portion 1078 in one or more directions perpendicular to a longitudinal axis 1040s of spine first and/or second portions 1072, 1074, and/or working channel and/or bending portion.

In some embodiments, bending of spine 1012 is actuated at a proximal portion of spine 1012. Referring to FIGS. 10A-C, for example, relative movement of spine rods 1072 and 1074 is actuated by relative axial movement of first rod tab 1054 and second rod tab 1058 where movement of first rod tab 1054 actuates movement of first spine rod 1072 and movement of second rod tab 1058 actuates movement of second spine rod 1074.

Referring now to FIG. 10E, in some embodiments, bending of spine bending portion 1078 is in one rotational direction in a bending plane, from a straight orientation. Where $\ominus$, for example, ranges between 0-175°, or 0-160°, or 0-140°, or 0-130°, or 0-120°, or 0-100°, or lower or higher or intermediate angles or ranges. In an exemplary embodiment, $\ominus$ ranges between 0° to about 130°.

In some embodiments, bending in the other rotational direction in the bending plane (e.g. where $\ominus$ is less than 0° is prevented by a mechanical stop. Where, in an exemplary embodiment, the mechanical stop is provided by a geometry of the lumen of first spine rod 1072 and a geometry of the second spine rod 1074. For example, in some embodiments, lumen 1072L of first spine rod 1072 is smaller than a portion of the second spine rod 1074, the geometry of lune 1072 preventing passage into the lumen of portion/s of the second spine rod 1074. Where the portion of the second spine rod 1074, for example, is a distal portion of the second spine rod 1074.

Alternatively, in some embodiments, bending is in both rotational directions in the bending plane, where ⊖, in some embodiments, ranges between 175°-175°, or 160°-160°, or 140°-140°, or 130°-130°, or 120°-120°, or 100°-100°, or lower or higher or intermediate angles or ranges. In some embodiments, the range of bending movement is symmetrical e.g. about the longitudinal axis 1040s of spine 1012. Alternatively, in some embodiments, the range of bending movement is asymmetrical where bending is possible to a higher degree in one rotational direction, in the bending plane, from a straight configuration (straight configuration e.g. as illustrated in FIG. 10A) than in the other rotational direction.

In some embodiments, relative movement between first spine rod 1072 and second spine rod 1074 is transferred to pivoting of bending portion 1078 by a joint portion 1096 which is coupled, in some embodiments, to both bending portion 1078 and second rod portion 1074.

In some embodiments, when spine 1012 is in a straight configuration, both spine rods 1072, 1074 and, in some embodiments, all spine portions (e.g. spine rods 1072, 1074, joint portion 1014 and bending portion 1078) are orientated with longitudinal axes parallel (or mostly parallel e.g. within 10° or 5° or 1° of parallel) to a longitudinal axis of spine 1012. A potential advantage of this being high rigidity of spine 1012, at least when spine 1012 is in a straight configuration.

In some embodiments, spine 1012 has a small profile, for example, where width 1082 and depth 1080 (e.g. cross sectional width and depth at least for a distal portion of the spine) are 0.1×0.1 mm–8×8 mm, or 0.5×0.5 mm–8×8 mm, or 0.5×0.5 mm–5×5 mm, or 0.5×0.5 mm–3×3 mm or, about 1.5×2 mm, or lower or higher or intermediate ranges or dimensions. In some embodiments, spine 1012 is wider than it is deep, for example, by 1.5-5, or 1-5-2 times, or lower or higher or intermediate multiplies or ratios.

In some embodiments, spine 1012 includes a small number of parts e.g. less than 15 parts, or less than 10 parts, or about 7 parts. A seven-part spine, for example, including first and second spine rods 1072, 1074, a bending portion 1078, a joint portion 1014 and three connectors between the portions 1072, 1074, 1078, 1014 (connectors not illustrated). In some embodiments, the connectors are pins (not illustrated). In some embodiments, spine 1012 includes less than seven parts, for example, spine 1012 lacking a joint portion where second spine rod 1074 is directly connected to bending 1078 portion. Potential advantages of a small number of spine parts include ease of sterilization and/or low cost.

In some embodiments, one or more spine portion is connected to another spine portion with a pin. Where, for example, movement is by pivoting around pin/s.

In some embodiments, one or more connections of spine portions are where a first spine portion includes hollow protrusion/s which fit into a indentations of a second spine portion, pivoting being around an axis of the indentations and/or protrusion/s. With this type of connection, in some embodiments, spine 1012 includes as few as four portions (e.g. first and second spine rods 1072, 1074, a bending portion 1078, and a joint portion 1014) or as few as three portions (e.g. when lacking a joint portion 1096).

FIG. 11A-B are simplified schematic section views of a portion of a device, according to some embodiments of the invention.

A dashed line illustrates a longitudinal axis 1140s of a sheath body 1110 and/or a longitudinal axis of tool body 1120 on FIGS. 11A-B. Where a proximal portion of the section view, along this axis, is at an upper left portion of the figures and a distal portion is at a lower right portion of the figures. In some embodiments, sectional views of FIG. 11A-B correspond to plane 684 of FIG. 6. The configuration of spine 612 of FIG. 6 (bent) corresponds to the section view illustrated in FIG. 11A. FIG. 11B, in some embodiments, illustrates a configuration where a spine 1112 e.g. corresponding to spine 612 FIG. 6 is not bent.

As described, for example regarding FIGS. 10A-E, in some embodiments, relative axial movement between first and second spine rods 1172 and 1174 bends spine 1112 and/or straightens spine 1112 from a bent configuration: In some embodiments, FIG. 11A (spine bent) shows the same section as FIG. 11B (spine straight), but where an axial space 1184 between first and second spine tabs 1158, 1154 has increased between FIG. 11A to FIG. 11B, showing relative axial movement between spine rods 1172, 1174.

In some embodiments, second rod tab 1158 is moved axially by rotation of spine actuation knob 1162. Where, in some embodiments, second rod tab 1158 is disposed within a helical groove 1164 of spine actuation knob 1162. Rotation of spine actuation knob 1162 moves second rob tab 1158 axially within spine actuation knob 1162, second rod tab 1158 moving within a helical groove 1164 of spine actuation knob 1162 (exemplary details of helical groove 1164 of spine actuation knob 1162 are illustrated in FIG. 11C).

In some embodiments, rotation of spine actuation knob 1162 moves second spine rod 1162 axially with respect to first spine rod 1172 (e.g. as opposed to spine actuation knob 1162 moving axially e.g. with respect to both spine rods 1172, 1174). In some embodiments, spine actuation knob 1162 is prevented from moving axially. For example, in an exemplary embodiment, spine actuation knob 1162 is held between capping portion 1152 and base portion 1150.

Where, in some embodiments, a flange 1197 of capping portion 1152 prevents axial movement of spine actuation knob 1162 distal of capping portion 1152. In some embodiments, capping portion 1152 and a base portion 1150 are attached, with spine actuation knob 1162 there between. In some embodiments, capping portion 1152 and base portions 1150 are attached by first spine rod 1172 and/or by an attachment portion 1156. In some embodiments, attachment portion 1156 is optional. In some embodiments, one or both of attachment portion 1156 and first spine rod 1174 are attached to capping portion 1153 and/or base portions 1150 by pins (e.g. pins 1167, 1169 illustrated in FIG. 11E). Where, in an exemplary embodiment, a pin 1167 passes through a first channel in capping portion 1153, through a channel in first spine rod 1172 and, optionally, through a second channel in capping portion 1153 located on the other side of first spine rod 1172. In some embodiments, similar attachment by pins (e.g. one or more pins per attachment) is used to attach first spine rod 1172 to base portion 1150 (e.g. by pins 1171 illustrated in FIG. 11E) and/or attachment portion 1156 to base portion 1150 (e.g. by pins 1173 illustrated in FIG. 11E).

FIG. 11C is a simplified schematic section view of a spine actuation knob 1162, according to some embodiments of the invention. In FIG. 11C helical groove 1164 of spine actuation knob 1162 is visible. A proximal portion of the section view of FIG. 11C is at an upper left portion of the figure and a distal portion is at a lower right portion of the figure.

Exemplary Locking of Spine Actuation

FIG. 11D is a simplified schematic section view of a spine bending locking knob 1166 according to some embodiments of the invention. Visible in FIG. 11D is a helical groove 1175 of spine bending locking knob 1162.

A proximal portion of the section view of FIG. 11D is at an upper left portion of the figure and a distal portion is at a lower right portion of the figure.

FIG. 11E is a simplified schematic view of a base portion 1150, according to some embodiments of the invention.

A proximal portion of the section view, of FIG. 11E is at a lower left portion of the figure and a distal portion is at an upper right portion of the figure.

In some embodiments, the working channel device system (e.g. working channel device system 100 FIG. 1A, working channel device system 500 FIG. 5D, working channel device system 600 FIG. 6, working channel device system 700 FIGS. 7A-B) includes a spine articulation lock. For example, the lock, when activated, preventing change in bending angle of the spine (e.g. spine 112 FIG. 1A, spine 512 FIG. 5D, spine 612 FIG. 6, spine 712 FIGS. 7A-B).

In some embodiments, locking is for a continuous range of bending angles of the spine. Alternatively, in some embodiments, locking is at a discrete number of bending angles of the spine. The lock, for example, including a ratchet mechanism.

In some embodiments, tool 1102 passes through a lumen 1177 of base portion 1150. In some embodiments, lumen 1177 of base portion 1150 has an increasing extent perpendicular to a longitudinal axis 1140*bp* of base portion in a proximal direction (e.g. lumen 1177 includes at least a proximal portion which is conical in shape). Potentially, the increasing radial extent of lumen 1177 eases insertion of tool 1102 into base portion 1150 and/or in some embodiments, enables a change in angle of a longitudinal axis 1140*t* of a body 1120 of tool 1102 with respect to sheath 1110.

In some embodiments, first spine rod 1172 is attached to base portion 1150 (e.g. by pins 1171).

In some embodiments, base portion 1150 includes a thread 1131 on which, in some embodiments, spine bending locking knob 1166 moves axially e.g. spine bending locking knob 1166 has a thread 1175 matching thread 1131.

FIG. 11F is a simplified schematic view of a portion of a working channel device, according to some embodiments of the invention. A dashed line illustrates a longitudinal axis 1140*s* of a sheath body 1110 and/or a longitudinal axis 1140*t* of tool body 1120 on FIG. 11F. Where a proximal portion of the section view, along this axis, is at an upper portion of the figures and a distal portion is at a lower portion of the figure.

In some embodiments, FIG. 11F shows a section taken of a working channel device system as illustrated by plane 686 in FIG. 6.

FIG. 11G is a simplified view of a connection portion 1188, according to some embodiments of the invention.

In some embodiments, a spine bending locking knob 1166 is rotated to prevent bending of the spine (e.g. spine 112 FIGS. 1A-C, spine 212 FIG. 2, spine 512 FIGS. 5A-D, spine 612 FIG. 6, spine 712 FIGS. 7A-D, spine 812 FIGS. 8A-B, spine 1012 FIGS. 10A-E), for example, by preventing rotation of spine actuation knob 1162.

In some embodiments, spine bending locking knob 1166 and spine actuation knob 1162 are attached by a connecting portion 1188 details of which are illustrated in FIG. 11G.

In some embodiments, rotation of spine bending locking knob 1166 moves spine bending locking knob 1166 axially with respect to spine actuation knob 1162. For example, matching threading between spine bending locking knob 1166 and base portion 1150 meaning rotation of spine bending locking knob 1166 moves it axially along base portion 1150.

In some embodiments, linear movement of spine bending locking knob 1166 (e.g. on base portion 1150) in a proximal direction pushes a connecting portion 1188 into a spring 1170. In some embodiments, connecting portion 1188 includes protrusion/s 1192 which fit into an annular channel (e.g. channel 79 illustrated in FIG. 11D) of locking knob 1166 so that axial movement of spine bending locking knob 1166 moves connecting portion 1188 axially in the same direction. The movement of connecting portion 1188 pushes spine actuation knob 1162 into capping portion 1152, increasing friction between the two and "locking" rotation of spine actuation knob 1162.

Exemplary Locking of Axial Movement of Tool

Referring now to FIG. 11F, in an exemplary embodiment, a lock prevents axial movement of sheath 1110.

In some embodiments, the working channel device system (e.g. working channel device system 100 FIG. 1A, working channel device system 500 FIG. 5D, working channel device system 600 FIG. 6, working channel device system 700 FIGS. 7A-B) includes locking which prevents axial movement between the sheath and tool (e.g. sheath 110 and tool 102 FIG. 1A, sheath 510 and tool 502 FIG. 5D, sheath 610 tool 602 FIG. 6, sheath 710 tool 702 FIGS. 7A-B. For example, preventing change in an extent of sheathing of the tool within the sheath and/or an extent of extension of the tool from the sheath.

In some embodiments, locking includes a friction lock. Where the lock, when engaged, in some embodiments, increases friction of axial movement between the sheath and tool.

Sheath 1110, in some embodiments, is fixed to capping portion 1152. In some embodiments, the lock includes elastic portion/s 1198 which, are urged into contact with base potion 1150 (which is attached to sheath 1110 e.g. by capping portion 1152) preventing axial movement of sheath 1110. Elastic portion/s in some embodiments, are part of handle portions e.g. elastic portions 1298*a*, 1298*b* illustrated in FIGS. 12D, 12F and 12G.

In some embodiments, elastic portion/s 1198 are pushed into contact with sheath 1110 by an axial movement lock portion 1101. Where, in some embodiments, axial movement lock portion 1101 applies a force which increases friction between elastic portion/s 1198 and base portion 1150. For example, an inner surface 1101*is* of portion 1101 applies an inwards radial force 1101F on elastic portion/s 1198. In some embodiments, the lock is biased in a locked position by an axial movement lock spring 1103, which, in some embodiments, relaxes to expand, pushing portion 1101 towards elastic portion/s 1198.

For example, in some embodiments, a user unlocks axial movement of the tool body 1120 with respect to sheath 1110 by retracting axial movement lock portion 1101 (e.g. proximally illustrated by arrow 1105). The proximal retraction of axial movement lock portion 1101, in some embodiments, means that elastic portion/s 1198 elastically relax to move away from contact with base portion 1150. Once unlocked, the user positions sheath 1110 axially with respect to tool body 1120 (e.g. by moving capping portion 1152 distally and/or proximally). Then, in some embodiments, the user releases axial movement lock portion 1101 to lock axial movement e.g. to re-lock axial movement.

Exemplary Tool End Effector Exemplary Actuation

FIG. 12A is a simplified schematic view of a working channel device handle, according to some embodiments of the invention.

FIG. 12B is a simplified schematic section view of a working channel device handle, according to some embodiments of the invention.

FIG. 12C is a simplified schematic section view of a working channel device handle, according to some embodiments of the invention.

FIG. 12D is a simplified schematic view of a portion of a working channel device handle, according to some embodiments of the invention.

FIG. 12E is a simplified schematic view of a portion of a working channel device handle, according to some embodiments of the invention.

FIG. 12F is a simplified schematic view of a portion of a working channel device handle, according to some embodiments of the invention.

FIG. 12G is a simplified schematic view of a working channel device handle, according to some embodiments of the invention.

In some embodiments, activation of a tool end effector (e.g. end effector 108 FIGs. 1A and 1C, end effector 208 FIG. 2, end effector 508 FIGS. 5A and 5C, end effector 608 FIG. 6, end effector 708 FIGS. 7A-D, end effector 808 FIGS. 8A-B is by changing tension on an elongated element 1211. In some embodiments, elongated element 1211 includes a wire and/or a cable. Where, in some embodiments, elongated element 1211 extends from tool end effector proximally e.g. to a handle 1213 of the working channel device system (e.g. handle 513 of working channel device system 500 FIG. 5D, handle 613 of working channel device system 600 FIG. 6, handle 713 of working channel device system 700 FIGS. 7A-B).

In some embodiments, tension on elongated element 1211 is changed by moving portion/s coupled to elongated element 1211. In an exemplary embodiment, elongated element 1211 is fixed axially to a holder portion 1215 where, in some embodiments, holder 1215 is disposed within handle 1213. In some embodiments, holder 1215 is moved (e.g. within the handle) to change tension on elongated element 1211, for example, in some embodiments, by axial movement of one or more buttons 1209 of holder 1215. Where, in some embodiments, buttons 1209 protrude out of an outer surface of handle 1213 (e.g. illustrated in FIG. 12A). In an exemplary embodiment, a user moves a tool actuation knob 1217 to move button portion/s 1209 within slits 1281 and thereby holder portion 1215 in an axial direction. Where button portions 1209, in some embodiments, each move axially within slits 1281 in handle body 1213.

In some embodiments, attachment 1283 of elongated portion 1211 to holder 1221 is adjustable, e.g. to adjust tension on elongated portion 1283 e.g. as illustrated by connection of elongated portion 1283 to holder 1215 in FIG. 12C where attachment 1283 is by pins 1283a and intermediate elements 1283b.

In some embodiments, the tool handle includes a first handle portion 1225 and a second handle portion 1227, as illustrated, for example, in FIGS. 12D-F.

Also visible in FIG. 12D and FIG. 12F are elastic portions 1298a, 1298b of e.g. as described, for example, in the section of this document entitled "Exemplary locking of axial movement of tool".

In some embodiments, handle portions 1225, 1227, are connected holding holder portion 1215 therebetween.

Referring back to FIG. 12C, in some embodiments, tool body 1220 (e.g. a proximal end of the tool body) is attached to handle 1213. For example, tool body 1220, in some embodiments, is pinned by a plate portion 1223 to handle first portion 1225. In some embodiments, tool body 1220 is fixed to handle 1213 so that rotation illustrated by arrow 1213a about a longitudinal axis of the handle 1240h rotates tool body 1220 (and thereby, in some embodiments, an end effector of the tool). Where rotation of handle 1213, in some embodiments, is illustrated by arrow 1213a on FIG. 12A.

FIG. 13 is a simplified view of a tool end effector 1308, according to some embodiments of the invention.

In some embodiments, end effector 1308 includes a stationary portion 1139 and a moveable portion 1335. In some embodiments, actuation of end effector 1308 is by changing tension on an elongated element 1311 coupled to moveable portion 1335 e.g. at a coupling channel 1337 of moveable portion 1335. In some embodiments, increasing tension on elongated element 1311 pivots moveable portion 1335 about pivot 1333 to increase a space between moveable portion 1335 and a stationary portion 1339 (e.g. open the end effector 1308). Where pivot 1333, in some embodiments is formed by geometries of the moveable portion 1335 and stationary portion 1339. In some embodiments, elongated element 1311 is axially rigid and moveable portion 1335 is returned (e.g. to close end effector 1308) by pushing distally with elongated element 1311. Alternatively or additionally, end effector 1308 includes an elastic portion 1343 which elastically returns moveable portion 1335 e.g. to close end effector 1308. For example, in some embodiments, elongated element 1311 is coupled to an elastic portion 1343 which is coupled to stationary portion 1339. For example, elastic portion 1343 deforming (e.g. stretching) when moveable portion 1335 pivots to open end effector 1308 and elastically relaxing to return the moveable portion 1335.

In some embodiments, end effector 1308 has a tapering and/or pointed portion 1341.

Additional Exemplary End Effectors

FIG. 14 is a simplified schematic of a grasper tool 1408, according to some embodiments of the invention.

In some embodiments, tool 1408 includes one or more joints 1443 e.g. where the end effector, in some embodiments is articulable to change an angle of the end effector with respect to a body of the tool adjacent to the end effector. In some embodiments, an end effector joint is in lieu of an end effector flexible portion.

FIG. 15 is a simplified schematic of a needle tool 1408, according to some embodiments of the invention.

In some embodiments, at least a portion of a tool body 1520 is flexible. In some embodiments, a majority and/or entire length of a tool body 1530 is flexible.

Exemplary Sheaths and Working Channels

FIG. 16 is a simplified schematic of a working channel device system 1600, according to some embodiments of the invention.

In some embodiments, working channel device 1606 includes a sheath 1610 and a spine 1612, where spine 1612 is disposed within sheath 1610, for example, coupled to an inside surface of the sheath 1610.

In some embodiments spine 1612 includes a joint 1614. In some embodiments, sheath 1610 includes a lumen 1616. In some embodiments, sheath 1610 includes a flexible portion 1618. In some embodiments, spine 1612 is coupled to sheath 1610 such that joint 1614 is positioned within a longitudinal extent of flexible portion 1618. In some embodiments, tool 1602 includes one or more features as illustrated in and/or described regarding FIG. 1C.

FIGS. 17-21 illustrate exemplary embodiments of sheaths including two lumens. For example, in some embodiments, a sheath includes more than one lumen, for example, 2-5 lumens. For example, a first lumen of a sheath housing a tool and a second lumen of the sheath housing the spine.

FIG. 17 is a simplified schematic of a sheath 1710, according to some embodiments of the invention.

In some embodiments, sheath 1710 both forms a lumen of a working channel device 1616 and encloses a spine 1712. Where a first lumen 1716 of the sheath is sized and/or shaped to house a tool and a second lumen 1745 of sheath 1710 houses a spine 1712.

In some embodiments, spine 1712 is bendable in a single bending plane (for example, as described r in the portion of this document describing FIG. 10E). In some embodiments, sheath 1710 and spine 1712 are connected (e.g. by the sheath 1710 itself when the sheath has two lumens 1716, 1745) such that a plane connecting a longitudinal axis of a first lumen 1716 is at an angle to the single bending plane 1712bp of spine 1712 where the angle is at least 10°, or at least 45°, or at about 90° or lower or higher or intermediate angles or ranges. A potential advantage being low interference of sheath 1710 in bending of spine 1712.

FIG. 18 is a simplified schematic of a sheath 1810, according to some embodiments of the invention.

In some embodiments, sheath 1810 both forms a lumen of a working channel device 1816 and encloses a spine 1812. Where a first lumen 1816 of sheath 1810 is sized and/or shaped to house a tool and a second lumen 1845 of sheath 1810 houses a spine 1812.

In some embodiments, spine 1812 is bendable in a single bending plane (for example, as described in the portion of this document describing FIG. 10E). In some embodiments, sheath 1810 and spine 1812 are connected (e.g. by sheath 1810 itself when sheath 1810 has at least two lumens 1816, 1845, such that a plane connecting a longitudinal axis of first lumen 1816 of sheath 1816 and a longitudinal axis of spine 1812 and/or second lumen 1845 is the same as (or is within 1-10° of) the single bending plane 1812bp of the spine 1812. Potentially, reducing a range of bending angles of the device (a range of angles of spine bending is reduced by the sheath). A potential advantage being low height of the device for use in narrow spaces e.g. between bones e.g. in a meniscus procedure.

FIG. 19 is a simplified schematic of a sheath 1910, according to some embodiments of the invention.

Where a first lumen 1916 of sheath 1910 is sized and/or shaped to house a tool (not illustrated) and a second lumen 1945 of sheath 1910 houses a spine 1912.

In some embodiments, sheath 1910 is elastic (e.g. elastic in a radial direction) for example, allowing bending of spine 1912. In some embodiments, sheath 1910 includes one or more openings, e.g. enabling protrusion of spine 1912 from sheath 1910. A potential benefit being reduced elasticity required of the sheath material.

FIG. 20 is a simplified schematic cross section of a sheath 2010, according to some embodiments of the invention. Where a first lumen 2016 of the sheath is sized and/or shaped to house a tool and a second lumen 2045 of the sheath houses a spine 2012.

FIG. 21 is a simplified schematic cross section of a sheath 2110, according to some embodiments of the invention. Where a first lumen 2116 of sheath 2110 is sized and/or shaped to house a tool (not illustrated) and a second lumen 2145 of the sheath houses a spine 2112.

FIGS. 22A-D are simplified schematics of sheath structures, according to some embodiments of the invention.

In some embodiments, the sheath is constructed from (or a portion of the length of the sheath is constructed from) an open spiral, e.g. as illustrated in the sheath cross section of FIG. 22A. In some embodiments, open spiral portion/s of the sheath are axially expandable.

In some embodiments, a sheath has different proprieties in different directions perpendicular to a longitudinal axis of the sheath e.g. different radial directions. FIG. 22B illustrates a sheath cross section where rigid half tubes 2253 are connected by flexible portions 2251 e.g. a plurality of flexible strings 2251. For example, the sheath remaining tubular with oval or circular cross section until experiencing an expanding force (e.g. applied by an object within the sheath e.g. a tool e.g. tool end effector) when at least a portion of the sheath expands e.g. to the configuration illustrated in FIG. 22B.

FIG. 22C, in some embodiments, illustrates a sheath 2210 where at least a portion of sheath 2210 is expandable in direction/s perpendicular to a longitudinal axis 2240s of sheath 2210. In some embodiments, sheath 2210 is a braided tube.

FIG. 22D, in some embodiments, illustrates a sheath including a flexible tube of connected discrete portions.

Exemplary Connection of Exemplary Spine to Exemplary Sheath

FIG. 23A is a simplified schematic of a distal portion of a spine 2312, according to some embodiments of the invention.

FIG. 23B is a simplified schematic of a distal portion of a working channel device 2306.

In some embodiments, the spine is attached to the sheath at a discrete number of locations, for example, by one or more connectors 2324.

In some embodiments, connection is between spine 2312 and one or more rigid portions of the sheath 2310, for example, where a flexible portion 2318 of the sheath 2310, in some embodiments, is not directly connected to spine 2312. In an exemplary embodiment, a distal end 2312d of spine 2312 is attached to a distal end 2310d of the sheath 2310 e.g. illustrated in FIG. 23B.

Alternatively or additionally, in some embodiments, a large proportion and/or a continuous portion of a spine is attached to a sheath. For example by an outer sheath and/or cover (not illustrated). For example, referring back to FIG. 17 where sheath 1710 includes two lumens 1716, 1745, a first lumen 1716 providing a working channel for a tool (not illustrated in FIG. 17) and second lumen 1745 for spine 1712.

Referring back to FIGS. 23A-B, in some embodiments, spine 2312 is inserted through lumens of attachments 2324 disposed on the sheath 2310. In some embodiments, the distal portion of spine 2312 includes an elastically bendable portion 2355 and a flange 2357 which prevent, in some embodiments, spine 2312 retracting (e.g. proximally) from distal attachment 2324a to the sheath. In some embodiments, one or more attachments (e.g. attachment 2324b and/or attachments other than the distalmost attachment 2324a) allow axial movement between sheath 2310 and spine 2312. Axial movement between sheath 2310 and spine 2312 potentially reducing stresses on the sheath 2310 and/or spine 2312 associated with different radii of curvature of the sheath flexible portion 2344 and a spine joint 2314.

Additional Exemplary Embodiments

Exemplary Spines

FIG. 24 is a simplified schematic of a distal portion of a spine 2412, according to some embodiments of the invention.

In some embodiments, a distal end 2491 of spine 2412 is blunt.

FIG. 25 is a simplified schematic of a distal portion of a spine 2512, according to some embodiments of the invention.

In some embodiments, spine 2512 includes an end effector 2508a. Where, for example, a spine moveable portion 2578 includes a sharp tip 2578a e.g. for cutting and/or piercing.

Exemplary Two Part Sheath

FIG. 26 is a simplified schematic of an exploded view of a working channel device 2606, according to some embodiments of the invention.

In some embodiments, working channel device includes a first portion 2659 and a second portion 2661. In some embodiments, a dashed line arrow 2689 illustrates connection of the two portions 2659, 2661.

In some embodiments, a first portion 2659 includes a spine 2612 connected to an inner sheath 2659 and a second portion 2661 includes an outer sheath 2663 with a connector 2624 to connect spine 2612 to second portion 2661. In some embodiments, connector 2524 is rigid. In some embodiments, inner sheath 2659 is non-flexible (e.g. rigid) and outer sheath 2663 is flexible. In some embodiments, working channel device 2606 when first portion 2659 is inserted into second portion 2661, section/s of outer sheath 2659 which do not overlap axially with inner sheath 2659 e.g. flexible section 2265 are flexible. In some embodiments, second portion 2661 is disposable while first portion 2659 is reusable e.g. sterilizable.

General

It is expected that during the life of a patent maturing from this application many relevant surgical tools will be developed and the scope of the term surgical tool is intended to include all such new technologies a priori.

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An arthroscopic surgical device comprising:
a body with a proximal end, a distal end, and a body longitudinal axis extending between said proximal end and said distal end, said body comprising:
an elongated sheath arranged along a sheath longitudinal axis, said sheath comprising:
a sheath flexible portion having a single articulatable joint;
an elongated spine arranged along a spine longitudinal axis, said spine connected to said sheath, said spine comprising a single spine joint;
wherein said spine is rigid in a direction of elongation of said spine;

wherein said sheath longitudinal axis and said spine longitudinal axis are aligned, for at least a portion of a sheath longitudinal length, wherein said single articulatable joint of said flexible portion axially overlaps with said single spine joint, bending said single spine joint thereby bending said single articulatable joint of said flexible portion;

wherein said spine comprises:
a first elongated spine rod;
a second elongated spine rod;
a distal portion of the spine, where said distal portion:
is attached to a distal end of said first spine rod at a first point on said distal portion; and
is attached to said second spine rod at a second point on said distal portion, spaced from said first point;
wherein axial movement of said first spine rod in a distal direction changes an angle of said distal portion with respect to long axes of said first and said second spine rod.

2. The arthroscopic surgical device of claim 1, wherein said lumen is sized and shaped to receive an arthroscopic tool.

3. The arthroscopic surgical device of claim 1, wherein said single spine joint is positioned in a distal portion of the spine.

4. The arthroscopic surgical device of claim 1, wherein said single spine joint is a single pivot joint.

5. The arthroscopic surgical device of claim 1, wherein said single spine joint is bendable, from a straight orientation in a single bending plane, by 0-130°.

6. The arthroscopic surgical device of claim 1, wherein said sheath flexible portion is radially expandable.

7. The arthroscopic surgical device of claim 1, comprising a first pivot joint, wherein said distal end of said first spine rod is pivotally attached at said first pivot joint to said distal portion.

8. The arthroscopic surgical device of claim 7, comprising a second pivot joint, wherein said distal end of said second spine rod is pivotally attached at said second pivot joint to said distal portion.

9. The arthroscopic surgical device of claim 1, wherein said second spine rod is at least partially housed within a lumen of said first spine rod.

10. The arthroscopic surgical device of claim 1, wherein relative movement between said first and said second spine rod is actuated at proximal portions of said rods.

11. The arthroscopic surgical device of claim 1, wherein said elongated sheath comprises a first sheath portion and a second sheath portion;
wherein said second sheath portion is sized and shaped to cover a distal portion of said first sheath portion and extend distally therefrom; and
where said elongated spine is connected to said first sheath portion.

12. The arthroscopic surgical device of claim 1, wherein said sheath includes a lumen running longitudinally through said sheath.

13. The arthroscopic surgical device of claim 1, wherein said axial movement of said first spine rod in the distal direction is from a first position in which said single spine joint is straight to a second position, in which said single spine joint is bent.

14. The arthroscopic surgical device of claim 1, wherein said axial movement of said first spine rod in the distal direction is from a first position to a second position, wherein said first spine rod is biased toward said first position.

15. An arthroscopic surgical device system comprising:
the arthroscopic surgical device of claim 1; and
an elongated surgical tool sized and shaped to move at least one of axially and rotatably within said lumen.

16. The arthroscopic surgical device system of claim 15, wherein said surgical tool comprises a tool flexible portion.

17. The arthroscopic surgical device system of claim 15, wherein said surgical tool is axially moveable with respect to said sheath, to position said tool flexible portion in an axially overlapping position with said sheath flexible portion, wherein said surgical tool is rotatable around a surgical tool longitudinal axis when a portion of said surgical tool is disposed within said lumen.

18. The arthroscopic surgical device system of claim 15, comprising a lock which locks bending of said spine.

19. The arthroscopic surgical device system of claim 15, comprising a lock which locks at least one of axial or rotational movement of said surgical tool with respect to said sheath.

20. The arthroscopic surgical device system of claim 15, comprising a controller for bending of said spine, located at a handle located at proximal portion of said system.

21. The arthroscopic surgical device system of claim 20, where said tool comprises an end effector;
wherein said surgical device system comprises a controller for actuation of said end effector located at said handle.

22. The arthroscopic surgical device system of claim 20, wherein one or more locks for locking of at least one of bending of said spine and locking of at least one of axial and rotational movement of said tool with respect to said sheath are located in said handle.

23.
A method of arthroscopic treatment comprising:
positioning an outlet of a working channel device within tissue of a subject, wherein the working channel device comprises:
a body with a proximal end, a distal end, and a body longitudinal axis extending between said proximal end and said distal end;
said body comprising:
an elongated sheath arranged along a sheath longitudinal axis, said sheath comprising:
a sheath flexible portion;
an elongated spine arranged along a spine longitudinal axis, said spine connected to said sheath, said spine comprising a single spine joint;
wherein said spine is rigid in a direction of elongation of said spine;
wherein said sheath longitudinal axis and said spine longitudinal axis are aligned, for at least a portion of a sheath longitudinal length,
wherein said flexible portion axially overlaps with said single_spine joint, bending said single spine joint thereby bending said flexible portion;
bending said working channel device to reposition said outlet; and
treating tissue at a treatment site within tissue of said subject with an arthroscopic tool accessing said treatment site from a lumen of said working channel and through said outlet;
wherein said spine comprises:
a first elongated spine rod;
a second elongated spine rod;
a distal portion of the spine, where said distal portion:
is attached to a distal end of said first spine rod at a first point on said distal portion; and is attached to said second spine rod at a second point on said distal portion, spaced from said first point;

wherein axial movement of said first spine rod in a distal direction changes an angle of said distal portion with respect to long axes of said first and said second spine rod.

24. (The method of claim 23, wherein said sheath is rigidized by said spine-, where said outlet is an outlet of said sheath; and wherein said bending comprises bending said spine at said single spine joint to bend said sheath.

25. A kit for arthroscopic treatment comprising:

the arthroscopic surgical device of claim 1; and at least one elongated surgical tool sized and shaped to move at least one of axially and rotatably within said lumen.

26. The kit for arthroscopic treatment of claim 25, wherein said elongated sheath comprises a first sheath portion and a second sheath portion;

wherein said second sheath portion is sized and shaped to cover a distal portion of said first sheath portion and extend distally therefrom; and where said elongated spine is connected to said first sheath portion.

27. The kit of claim 26, wherein said first sheath portion is rigid and wherein said sheath flexible portion is part of said second sheath portion.

* * * * *